(12) United States Patent
Chanteux et al.

(10) Patent No.: US 11,286,266 B2
(45) Date of Patent: Mar. 29, 2022

(54) 1-IMIDAZOTHIADIAZOLO-2H-PYRROL-5-ONE DERIVATIVES

(71) Applicant: UCB Biopharma SRL, Brussels (BE)

(72) Inventors: Hugues Chanteux, Brussels (BE);
Yannick Quesnel, Brussels (BE);
Claude Delatour, Brussels (BE);
Laurent Provins, Brussels (BE)

(73) Assignee: UCB Biopharma SRL

( * ) Notice: Subject to any disclaimer, the term of this patent is extended or adjusted under 35 U.S.C. 154(b) by 0 days.

(21) Appl. No.: 17/052,978

(22) PCT Filed: May 6, 2019

(86) PCT No.: PCT/EP2019/061498
§ 371 (c)(1),
(2) Date: Nov. 4, 2020

(87) PCT Pub. No.: WO2019/215062
PCT Pub. Date: Nov. 14, 2019

(65) Prior Publication Data
US 2021/0107922 A1  Apr. 15, 2021

(30) Foreign Application Priority Data
May 8, 2018  (EP) ..................................... 18171130

(51) Int. Cl.
*C07D 513/04* (2006.01)
(52) U.S. Cl.
CPC .................. *C07D 513/04* (2013.01)
(58) Field of Classification Search
CPC .................................................. C07D 513/04
USPC ....................................................... 514/363
See application file for complete search history.

(56) References Cited

U.S. PATENT DOCUMENTS 11,155,566 B2 * 10/2021 Provins ................ C07D 513/04

FOREIGN PATENT DOCUMENTS

| WO | WO 2006/128692 | 12/2006 |
| WO | WO 2008/132139 | 11/2008 |
| WO | WO 2011/047860 | 4/2011 |

OTHER PUBLICATIONS

International Search Report dated Jul. 9, 2019 for International Application No. PCT/EP2019/061498, 2 pages.

* cited by examiner

*Primary Examiner* — Kahsay Habte
(74) *Attorney, Agent, or Firm* — McDonnell Boehnen Hulbert & Berghoff LLP

(57) ABSTRACT

The present invention relates to 1-imidazothiadiazolo-2H-pyrrol-5-one derivatives, processes for preparing them, pharmaceutical compositions containing them and their use as pharmaceuticals.

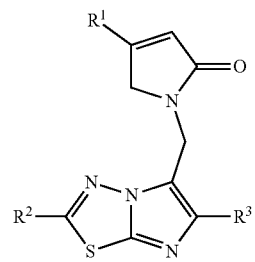

13 Claims, No Drawings

1-IMIDAZOTHIADIAZOLO-2H-PYRROL-5-ONE DERIVATIVES

CROSS-REFERENCE TO RELATED APPLICATIONS

This application is a U.S. national phase of International Application No. PCT/EP2019/061498, filed May 6, 2019, which claims priority from European Patent Application No. EP18171130.0, filed May 8, 2018, the disclosure of each of which is hereby incorporated by reference in its entirety.

INTRODUCTION

The present invention relates to 1-imidazothiadiazolo-2H-pyrrol-5-one derivatives, processes for preparing them, pharmaceutical compositions containing them and their use as pharmaceuticals.

It is known from the literature (Kaminski et al. in *Neuropharmacology*, 54, (2008) 715) that a functional correlation between SV2A binding affinity and anticonvulsant potency exists and that SV2A protein appears to exert a role in epilepsy pathophysiology (Löscher et al. in CNS drugs, October 2016).

Several SV2A ligands have been described in the State of the Art including those described hereafter in our co-pending patent applications.

WO2011/047860 discloses 2-oxo-1-pyrrolidinyl imidazothiadiazole derivatives compounds of the following formula A:

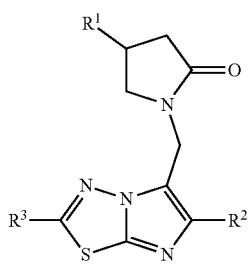

wherein:

$R^1$ is a $C_{1-4}$ alkyl containing at least one halogen substituent;

$R^2$ is either a halogen or a $C_{1-4}$ alkyl containing at least one halogen substituent;

$R^3$ is a $C_{1-4}$ alkyl containing at least one hydroxy or alkoxy substituent.

Anti-epileptic compounds of formula (B) are disclosed in WO 2008/132139:

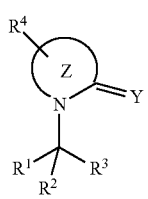

wherein

Y is O or S;

R1 is hydrogen or C1-6 alkyl;

R2 is hydrogen;

R3 is —CONR5R6, —COR7, an imidazolyl, an imidazopyridinyl, an imidazopyridazinyl;

R5, R6 are the same or different and are independently selected from hydrogen and C1-6 alkyl;

R7 is C1-6 alkyl;

Z is a monocyclic or bicyclic heterocyclic moiety selected from the group consisting of imidazolidin-1-yl, 1,3-oxazolidin-3-yl, 2,5-dihydro-1H-pyrrol-1-yl, 1,3-thiazol-3(2H)-yl, 1,3-thiazolidin-3-yl, piperidin-1-yl, azepan-1-yl, 5,6-dihydro-4H-thieno[3,2-b]pyrrol-4-yl, hexahydro-4H-thieno[3,2-b]pyrrol-4-yl, 2,3-dihydro-1H-thieno[3,4-b]pyrrol-1-yl, 1,3-benzothiazol-3(2H)-yl, 1,3-benzoxazol-3(2H)-yl, pyrazolo[1,5-a]pyridin-1(2H)-yl, 3,4-dihydroisoquinolin-2(1H)-yl, 3,4-dihydroquinolin-1(2H)-yl, 1,3,4,5-tetrahydro-2H-2-benzazepin-2-yl, 1,2,4,5-tetrahydro-3H-3-benzazepin-3-yl.

In a specific embodiment of WO 2008/132139 the Z=Y moiety in formula (B) could be:

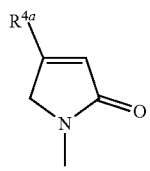

The compounds as described here above have been described for use as a medicament, in the treatment of epilepsy, epileptogenesis, seizure disorders, convulsions, in particular for refractory seizures.

Despite the availability of anti-epileptic drugs there is still a persistent problem in seizure control which arises with those patients who do not at all or only insufficiently respond to currently available treatments.

Those patients are viewed as being refractory to treatment and represent a considerable challenge for the medical community. It is estimated that about 30% of epilepsy patients are to be classified as being refractory. Hence, there is a need to develop new medications that specifically target this population of patients.

In addition, a problem which can be faced when developing compounds for use in therapy is the capacity for certain compounds to induce CYP450 enzymes. The induction of such enzymes may impact the exposure of such compounds or of other compounds which could be co-administered therewith to a patient, thereby potentially altering their respective safety or efficacy. It is therefore desirable to develop compounds which also minimize such potential for induction.

SUMMARY OF THE INVENTION

The present invention provides 1-imidazothiadiazolo-2H-pyrrol-5-one derivatives having the formula (I), their geometrical isomers, enantiomers, diastereoisomers, isotopes and mixtures, or a pharmaceutically acceptable salt thereof,

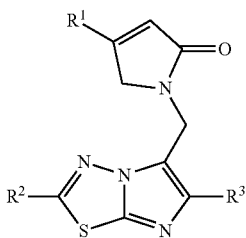

(I)

Further aspects of the invention will become apparent from the detailed description.

DETAILED DESCRIPTION OF THE INVENTION

The present invention relates to 1-imidazothiadiazolo-2H-pyrrol-5-one derivatives according to formula (I),

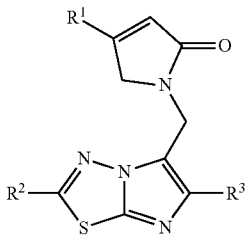

(I)

wherein $R^1$ is a $C_{1-4}$ alkyl or a $C_{3-5}$ cycloalkyl, either of which groups are optionally substituted by one or more halogen substituents;

$R^2$ is a $C_{1-4}$ alkyl substituted by one hydroxy or alkoxy substituent;

$R^3$ is a halogen; or $C_{1-4}$ alkyl or a $C_{3-4}$ cycloalkyl, either of which groups are optionally substituted by one or more halogen atoms.

Also comprised within the scope of the present invention are tautomers, geometrical isomers, enantiomers, diastereomers, isotopes, and mixtures, or a pharmaceutically acceptable salt of compounds of formula (I) as well as any deuterated variant.

The compounds according to formula (I) are therefore distinct from the compounds disclosed in the State of the Art.

In one embodiment, $R^1$ is a $C_{1-4}$ alkyl optionally substituted by one or more halogen substituents. In a first aspect of this embodiment, $R^1$ is an unsubstituted $C_{1-4}$ alkyl. In a second aspect of this embodiment, $R^1$ is a $C_{1-4}$ alkyl substituted by one or more halogen. Suitably, in this particular aspect, the halogen substituent is a chloro or a fluoro substitutent.

In another embodiment, $R^1$ is a $C_{3-5}$ cycloalkyl optionally substituted by one or more halogen substituents. In a first aspect of this embodiment, $R^1$ is an unsubstituted $C_{3-5}$ cycloalkyl. In a second aspect of this embodiment, $R^1$ is a $C_{3-5}$ cycloalkyl substituted by one or more halogen. Suitably, in this particular aspect, the halogen substituent is a fluoro substituent.

In a specific embodiment, $R^1$ is a $C_{1-4}$ alkyl substituted by one or more halogen substituents. In a particular aspect of this specific embodiment, $R^1$ is a $C_{1-4}$ alkyl substituted by one or more fluoro substituents.

Suitable examples of $R^1$ groups include, n-propyl, 2,2-difluoropropyl, 2-chloro-2,2-difluoroethyl, a 2,2-difluoroethyl, 2,2,2-trifluoroethyl, 3,3,3-trifluoropropyl 2-fluoroethyl and 2,2-diflurorocyclopropyl.

Particular examples of $R^1$ groups include n-propyl, 2-chloro-2,2-difluoroethyl, 2,2-difluoropropyl, 3,3,3-trifluoropropyl, 2,2,2-trifluoroethyl and 2,2-difluorocyclopropyl. In a preferred embodiment, $R^1$ is 3,3,3-trifluoropropyl or 2,2-diflurorocyclopropyl.

In one embodiment, $R^2$ is a $C_{1-4}$ alkyl substituted by one hydroxy. In another embodiment, $R^2$ is a $C_{1-4}$ alkyl substituted by one alkoxy substituent. In a particular aspect of this embodiment, $R^2$ is a $C_{1-4}$ alkyl substituted by a methoxy substituent.

In a specific embodiment, $R^2$ is a hydroxymethyl or a methoxymethyl

In a preferred embodiment, $R^2$ is methoxymethyl.

In a first embodiment, $R^3$ is a $C_{1-4}$ alkyl optionally substituted by one or more halogen atoms. In a first aspect of this embodiment, $R^3$ is an unsubstituted $C_{1-4}$ alkyl. In a second aspect of this embodiment, $R^3$ is a $C_{1-4}$ alkyl substituted by one or more halogen atoms. Suitably in this particular aspect, $R^3$ is a $C_{1-4}$ alkyl substituted by one or more fluoro atoms.

In a second embodiment, $R^3$ is a $C_{3-4}$ cycloalkyl optionally substituted by one or more halogen atoms. In a first aspect of this embodiment, $R^3$ is an unsubstituted $C_{3-4}$ cycloalkyl. In a second aspect of this embodiment, $R^3$ is a $C_{3-4}$ cycloalkyl substituted by one or more halogen atoms. Suitably in this particular aspect, $R^3$ is a $C_{3-4}$ cycloalkyl substituted by one or more fluoro atoms.

In a third embodiment, $R^3$ is a halogen. In a particular aspect of this embodiment, $R^3$ is chloro.

Suitable examples of $R^3$ include methyl, difluoromethyl, chloro, trifluoromethyl and 1-flurocyclopropyl.

In a preferred embodiment, $R^3$ is methyl or difluoromethyl.

All combinations of the above embodiments and examples of $R^1$, $R^2$, and $R^3$ groups are encompassed within the scope of the present invention.

In a further specific embodiment, compounds of formula (I) are those wherein:

$R^1$ is $C_{1-4}$ alkyl or $C_{3-5}$ cycloalkyl, either of which groups is optionally substituted by one or more halogen substituents;

$R^2$ is a $C_{1-4}$ alkyl substituted by a alkoxy substituent; and $R^3$ is a $C_{1-4}$ alkyl substituted by one or more halogen atoms.

Specific compounds according to the present invention are those selected from the group consisting of:

1-[[2-(methoxymethyl)-6-(trifluoromethyl)imidazo[2,1-b][1,3,4]thiadiazol-5-yl]methyl]-3-propyl-2H-pyrrol-5-one;

1-[[2-(methoxymethyl)-6-(trifluoromethyl)imidazo[2,1-b][1,3,4]thiadiazol-5-yl]methyl]-3-(2,2,2-trifluoroethyl)-2H-pyrrol-5-one;

1-[[2-(methoxymethyl)-6-(trifluoromethyl)imidazo[2,1-b][1,3,4]thiadiazol-5-yl]methyl]-3-(3,3,3-trifluoropropyl)-2H-pyrrol-5-one;

1-[[2-(methoxymethyl)-6-methyl-imidazo[2,1-b][1,3,4]thiadiazol-5-yl]methyl]-3-propyl-2H-pyrrol-5-one;

1-[[6-chloro-2-(methoxymethyl)imidazo[2,1-b][1,3,4]thiadiazol-5-yl]methyl]-3-(2,2,2-trifluoroethyl)-2H-pyrrol-5-one;

1-[[6-chloro-2-(methoxymethyl)imidazo[2,1-b][1,3,4]thiadiazol-5-yl]methyl]-3-propyl-2H-pyrrol-5-one;

1-[[6-chloro-2-(methoxymethyl)imidazo[2,1-b][1,3,4]thia-
diazol-5-yl]methyl]-3-(3,3,3-trifluoropropyl)-2H-pyrrol-
5-one;
1-[[6-(difluoromethyl)-2-(methoxymethyl)imidazo[2,1-b]
[1,3,4]thiadiazol-5-yl]methyl]-3-propyl-2H-pyrrol-5-one;
1-[[6-(difluoromethyl)-2-(methoxymethyl)imidazo[2,1-b]
[1,3,4]thiadiazol-5-yl]methyl]-3-(2,2,2-trifluoroethyl)-
2H-pyrrol-5-one.
1-[[2-(methoxymethyl)-6-methyl-imidazo[2,1-b][1,3,4]
thiadiazol-5-yl]methyl]-3-(2,2,2-trifluoroethyl)-2H-pyr-
rol-5-one;
1-[[6-(difluoromethyl)-2-(methoxymethyl)imidazo[2,1-b]
[1,3,4]thiadiazol-5-yl]methyl]-3-(2,2,2-trifluoroethyl)-
2H-pyrrol-5-one;
1-[[6-(1-fluorocyclopropyl)-2-(methoxymethyl)imidazo[2,
1-b][1,3,4]thiadiazol-5-yl]methyl]-3-(2,2,2-trifluoro-
ethyl)-2H-pyrrol-5-one;
3-(2-chloro-2,2-difluoro-ethyl)-1-[[2-(methoxymethyl)-6-
(trifluoromethyl)imidazo[2,1-b][1,3,4]thiadiazol-5-yl]
methyl]-2H-pyrrol-5-one;
1-[[2-(methoxymethyl)-6-methyl-imidazo[2,1-b][1,3,4]
thiadiazol-5-yl]methyl]-3-(3,3,3-trifluoropropyl)-2H-pyr-
rol-5-one;
1-[[6-(difluoromethyl)-2-(methoxymethyl)imidazo[2,1-b]
[1,3,4]thiadiazol-5-yl]methyl]-3-(3,3,3-trifluoropropyl)-
2H-pyrrol-5-one;
3-(2,2-difluoropropyl)-1-[[2-(methoxymethyl)-6-(trifluo-
romethyl)imidazo[2,1-b][1,3,4]thiadiazol-5-yl]methyl]-
2H-pyrrol-5-one;
1-[[6-(difluoromethyl)-2-(methoxymethyl)imidazo[2,1-b]
[1,3,4]thiadiazol-5-yl]methyl]-3-(2,2-difluoropropyl)-
2H-pyrrol-5-one;
3R-(2,2-difluorocyclopropyl)-1-[[2-(methoxymethyl)-6-
(trifluoromethyl)imidazo[2,1-b][1,3,4]thiadiazol-5-yl]
methyl]-2H-pyrrol-5-one;
3S-(2,2-difluorocyclopropyl)-1-[[2-(methoxymethyl)-6-(tri-
fluoromethyl)imidazo[2,1-b][1,3,4]thiadiazol-5-yl]
methyl]-2H-pyrrol-5-one;
1-[[2-(methoxymethyl)-6-methyl-imidazo[2,1-b][1,3,4]
thiadiazol-5-yl]methyl]-3R-[2,2-difluorocyclopropyl]-
2H-pyrrol-5-one;
1-[[2-(methoxymethyl)-6-methyl-imidazo[2,1-b][1,3,4]
thiadiazol-5-yl]methyl]-3S-[2,2-difluorocyclopropyl]-
2H-pyrrol-5-one;
1-[[6-(difluoromethyl)-2-(methoxymethyl)imidazo[2,1-b]
[1,3,4]thiadiazol-5-yl]methyl]-3R-[2,2-difluorocyclopro-
pyl]-2H-pyrrol-5-one;
1-[[6-(difluoromethyl)-2-(methoxymethyl)imidazo[2,1-b]
[1,3,4]thiadiazol-5-yl]methyl]-3S-[2,2-difluorocyclopro-
pyl]-2H-pyrrol-5-one;
3-(2,2-difluoropropyl)-1-[[2-(methoxymethyl)-6-methyl-
imidazo[2,1-b][1,3,4]thiadiazol-5-yl]methyl]-2H-pyrrol-
5-one;
1-[[2-(hydroxymethyl)-6-methyl-imidazo[2,1-b][1,3,4]thia-
diazol-5-yl]methyl]-3-(3,3,3-trifluoropropyl)-2H-pyrrol-
5-one;
1-[[6-(difluoromethyl)-2-(hydroxymethyl)imidazo[2,1-b][1,
3,4]thiadiazol-5-yl]methyl]-3-(3,3,3-trifluoropropyl)-2H-
pyrrol-5-one; and
1-[[6-(difluoromethyl)-2-(hydroxymethyl)imidazo[2,1-b][1,
3,4]thiadiazol-5-yl]methyl]-3-(2,2,2-trifluoroethyl)-2H-
pyrrol-5-one.

The following paragraphs provide definitions of the various chemical moieties that make up the compounds according to the invention and are intended to apply uniformly throughout the specification and claims unless an otherwise expressly set out definition provides a broader definition.

"$C_{1-4}$ alkyl" refers to alkyl groups having 1 to 4 carbon atoms. This term is exemplified by groups such as methyl, ethyl, n-propyl, isopropyl, n-butyl, isobutyl, tert-butyl. "$C_{1-4}$ alkyl" groups may be substituted by one or more substituents selected from halogen, hydroxy or alkoxy.

The term "$C_{3-5}$ cycloalkyl" as used herein refers to monovalent groups of 3 to 5 carbon atoms derived from a saturated monocyclic hydrocarbon. Illustrative $C_{3-5}$ cycloalkyl groups include cyclopropyl, cyclobutyl, and cyclopentyl. Examples of $C_{3-5}$ cycloalkyl groups are $C_{3-4}$ cycloalkyl which refer to groups having 3 to 4 carbon atoms. Illustrative $C_{3-4}$ cycloalkyl groups are cyclopropyl and cyclobutyl.

Any moiety "H" in formula (I) may be the isotope hydrogen, deuterium or tritium.

"Hydroxy" represents a group of formula —OH.

"Alkoxy" refers to the group —O—R where R includes "$C_{1-4}$ alkyl".

"Halogen" refers to fluoro, chloro, bromo and iodo atoms, preferably fluoro and chloro.

The "pharmaceutically acceptable salts" according to the invention include therapeutically active, non-toxic acid or base salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula (I) and their salts can be in the form of a solvate, which is included within the scope of the present invention. Such solvates include for example hydrates, alcoholates and the like.

Compounds of formula (I) and/or their intermediates may have at least one stereogenic center in their structure. This stereogenic center may be present in a R or a S configuration, said R and S notation is used in correspondence with the rules described in Pure Appl. Chem., 45 (1976) 11-30. The invention thus also relates to all stereoisomeric forms such as enantiomeric and diastereoisomeric forms of the compounds of formula (I) or mixtures thereof (including all possible mixtures of stereoisomers). With respect to the present invention reference to a compound or compounds is intended to encompass that compound in each of its possible isomeric forms and mixtures thereof, unless the particular isomeric form is referred to specifically. The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

The compounds of formula (I) according to the invention can be prepared analogously to conventional methods as understood by the person skilled in the art of synthetic organic chemistry.

According to one embodiment, compounds having the general formula (I) wherein $R^2$ is a $C_{1-4}$ alkyl substituted by one alkoxy substituent may be prepared by reductive amination of a hydroxylactone of formula (III) with an amine of formula (II) according to the equation:

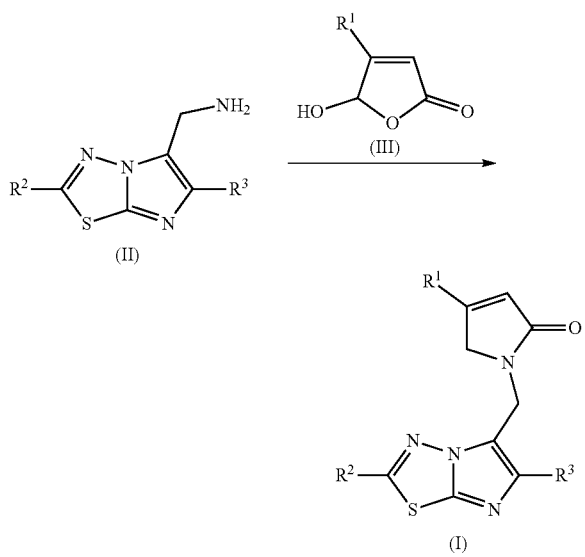

wherein $R^1$ and $R^3$ have the same definitions as defined above for compounds of formula (I).

This reaction may be performed according to procedures described in patent applications WO 01/62726, WO 2006/128792 and WO 2008/132139.

Compounds of formula (III) may be prepared according to methods described in patent applications WO 01/62726 or WO 2006/128792 or according to any method known to the person skilled in the art.

Compounds of formula (II) wherein $R^2$ is a $C_{1-4}$ alkyl substituted by one alkoxy substituent may be prepared by reduction of a compound of formula (IV) according to the equation:

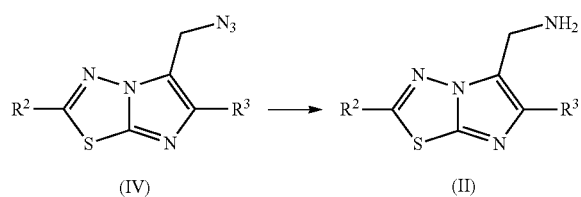

wherein $R^3$ has the same definitions as defined above for compounds of formula (I).

This reaction may be performed using a reducing agent such as triphenylphosphine in in a THF/water mixture at room temperature or according to any method known to the person skilled in the art.

Compounds of formula (IV) wherein $R^2$ is a $C_{1-4}$ alkyl substituted by one alkoxy substituent may be prepared by transformation of a compound of formula (V) according to the equation:

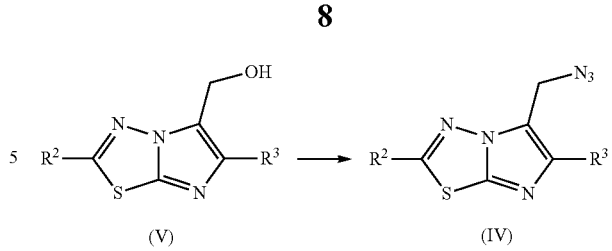

wherein $R^3$ has the same definitions as defined above for compounds of formula I.

This reaction may be performed in a two-steps sequence by treatment of compounds (V) with a sulfonyl chloride such as methanesulfonyl chloride in the presence of a base such as N,N-diisopropylethylamine in dichloromethane at 0° C., or according to any other method known to the person skilled in the art, followed by treatment of the intermediate with an azide derivative such as sodium azide in DMF at 0° C.

Alternatively, compounds (II) may be prepared in a three-steps sequence by treatment of compounds (V) with a sulfonyl chloride such as methanesulfonyl chloride in the presence of a base such as N,N-diisopropylethylamine or a chlorinating agent such as thionyl chloride, in dichloromethane at 0° C., or according to any other method known to the person skilled in the art, followed by treatment of the intermediate with hexamethylenetetramine and subsequent acid hydrolysis of the intermediate quaternary ammonium salt.

Compounds of formula (V) wherein $R^2$ is a $C_{1-4}$ alkyl substituted by one alkoxy substituent may be prepared by hydroxymethylation of a compound of formula (VI) according to the equation:

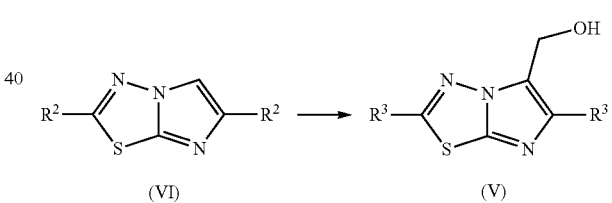

wherein $R^3$ has the same definition as defined above for compounds of formula (I).

This reaction may be performed using a formylating agent such as paraformaldehyde under acidic conditions in a polar solvent such as dioxane at 100° C., or according to any other method known to the person skilled in the art.

Compounds of formula (VI) wherein $R^2$ is a $C_{1-4}$ alkyl substituted by one alkoxy substituent may be synthesized by reaction of a compound of formula (VII) with a bromo derivative of formula (VIII) according to the equation:

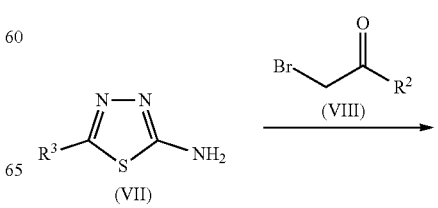

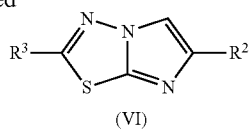

(VI)

wherein $R^3$ has the same definition as described above for compounds of formula (I).

This reaction can be performed using procedures described in the literature or known to the person skilled in the art.

Compounds of formula (VII) and of formula (VIII) are either commercially available or may be synthesized according to any method known to the person skilled in the art.

According to another embodiment, compounds of formula (I) wherein $R^2$ is a $C_{1-4}$ alkyl substituted by one alkoxy substituent may be synthesized by reaction of a compound of formula (V) with an pyrrolone of formula (IX) according to the equation:

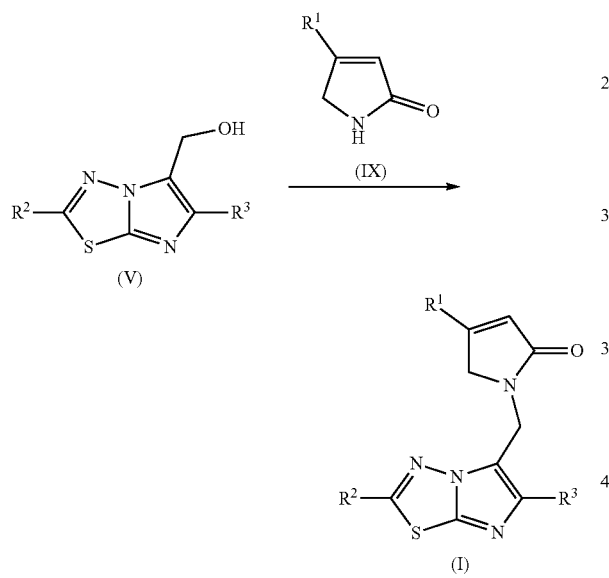

wherein $R^1$ and $R^3$ have the same definitions as defined above for compounds of formula (I).

This reaction may be performed using an acid such as p-toluenesulfonic acid in an aprotic solvent such as sulfolane at high temperature.

Compounds of formula (IX) may be prepared by deprotection of a compound of formula (X) according to the equation:

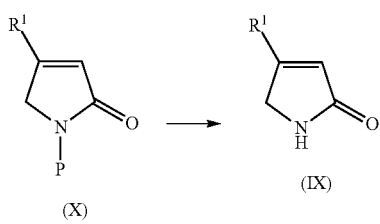

Wherein $R^1$ has the same definition as defined above for compounds of formula (I) and P is a protecting group such as an optionally substituted benzyl group.

This reaction may be performed according to any standard deprotection method known to the person skilled in the art.

Compounds of formula (X) may be prepared by reductive amination of a hydroxylactone of formula (III) with an amine of formula (XI)

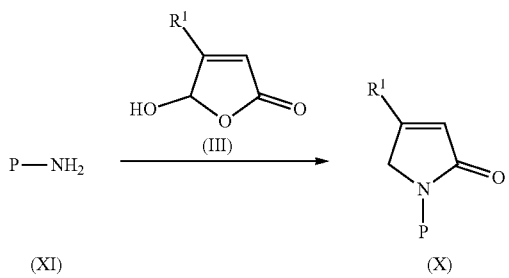

Wherein $R^1$ has the same definition as defined above for compounds of formula (I) and P is a protecting group such as an optionally substituted benzyl group.

This reaction may be performed according to procedures described in patent applications WO 01/62726, WO2006/128792 and WO2008/132139.

According to another embodiment, compounds of formula (I) wherein $R^2$ is a $C_{1-4}$ alkyl substituted by one alkoxy substituent may be synthesized by a Friedel-Crafts-type reaction of a compound of formula (VI) with a pyrrolone of formula (XII) according to the equation:

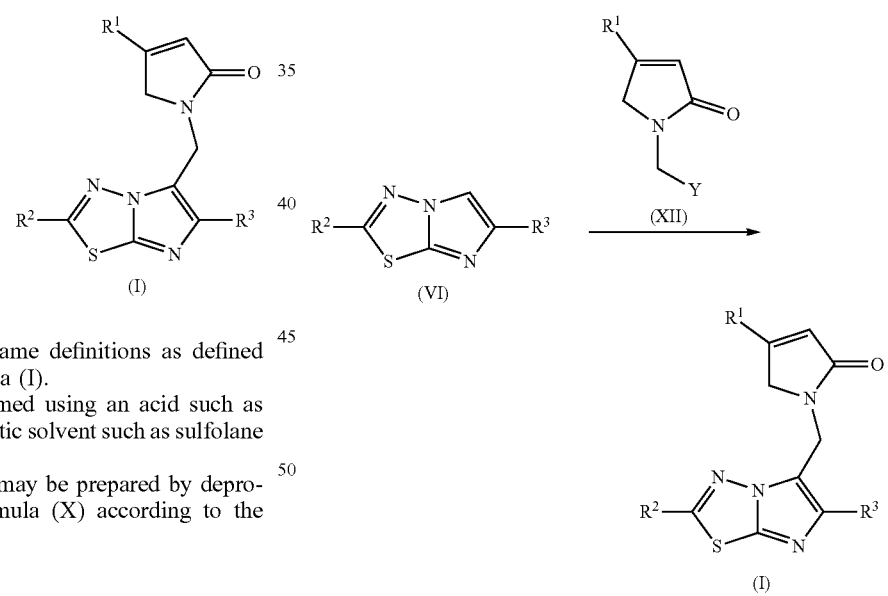

wherein $R^1$ and $R^3$ have the same definitions as defined above for compounds of formula (I).

This reaction can be performed with pyrrolones of formula (XII) bearing a leaving group (Y) such as a chlorine atom or a p-toluenesulfonyl group, in the presence of a Lewis acid such as zinc chloride or ferric chloride in a polar solvent such as sulfolane or dioxane at temperatures ranging from 100-120° C., or according to any procedure described in the literature or known to the person skilled in the art.

Compounds of formula (XII) may be prepared from the corresponding pyrrolones of formula (IX) according to the methods described in PCT patent application WO2006/128693 or according to any other method known to the person skilled in the art.

Alternatively, compounds of formula (I) wherein $R^2$ is a $C_{1-4}$ alkyl substituted by one alkoxy substituent may be synthesized by oxidation of a compound of formula (XIII) according to the equation:

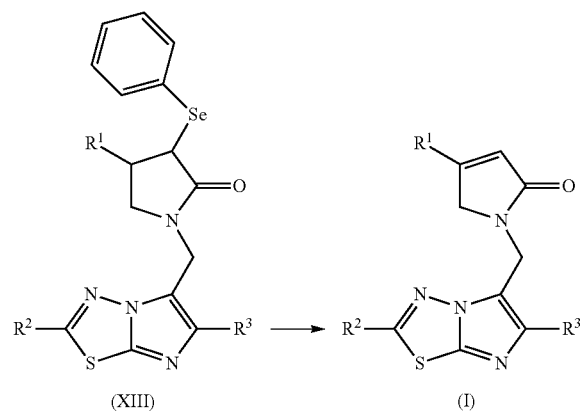

wherein $R^1$ and $R^3$ have the same definitions as defined above for compounds of formula (I). This reaction can be performed using an oxidizing agent such as sodium periodate in a polar solvent such as methanol at room temperature or by any method known to the person skilled in the art.

Compounds of formula (XIII) wherein $R^2$ is a $C_{1-4}$ alkyl substituted by one alkoxy substituent may be prepared by reaction of a compound of formula (V) with a pyrrolidone of formula (XIV) according to the equation:

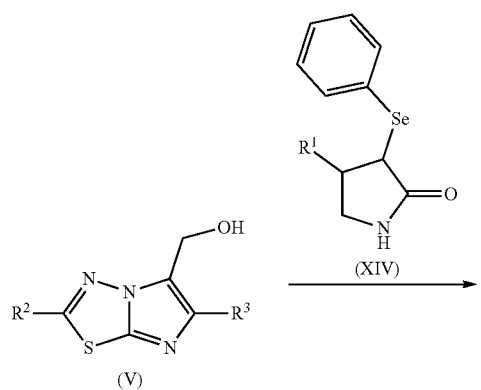

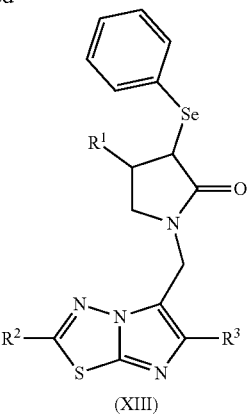

This reaction may be performed using an acid such as p-toluenesulfonic acid in an aprotic solvent such as sulfolane at high temperature.

Pyrrolidones of formula (XIV), wherein $R^1$ has the same definitions as defined above for compounds of formula (I), may be synthesized in a three-steps sequence by deprotection of a pyrrolidone of formula (XV) obtained by selenylation of a protected pyrrolidone (XVI) according to the equation:

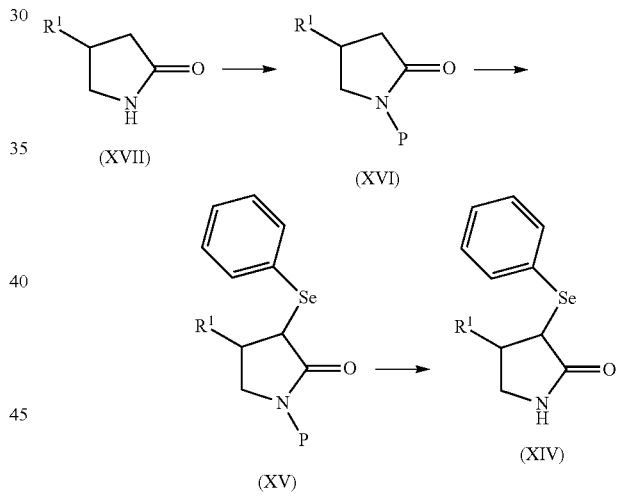

The protection-deprotection steps may be performed by any method known to the person skilled in the art. The selenylation reaction may be performed by deprotonation using a strong base such as lithium bis(trimethylsilyl)amide or lithium diisopropylamide in a polar solvent such a tetrahydrofuran at low temperature such as −78° C., followed by trapping of the enolate by a selenylating agent such as phenylselenenyl chloride or bromide.

Pyrrolidones (XVII) or (XVI) may be prepared according to methods described in patent applications WO2006/128792 or WO2011/047860 or according to any method known to the person skilled in the art.

Compounds of formula (I) wherein $R^2$ is a $C_{1-4}$ alkyl substituted by one hydroxy substituent may be prepared by dealkylation of compounds of formula (I) wherein $R^2$ is a $C_{1-4}$ alkyl substituted by one alkoxy substituent. This reaction may be performed using a dealkylation reagent such as boron tribromide or trichloride in a non-polar solvent such as dichloromethane at room temperature or according to any method known by the person skilled in the art.

The compounds of the present invention are beneficial for the treatment of epilepsy, epileptogenesis, seizure disorders, convulsions, in particular, of refractory seizures.

Hence, in another embodiment, the present invention provides a compound of formula (I) as defined above, or a pharmaceutically acceptable salt thereof, for use as a medicament.

In one aspect of that embodiment, the present invention also provides a compound of formula (I) as defined above, or a pharmaceutically acceptable salt thereof, for use in the treatment and/or prevention of epilepsy, epileptogenesis, seizure disorders, convulsions, in particular, of refractory seizures.

In a further embodiment, the present invention provides the use of a compound of formula (I) as defined above, or a pharmaceutically acceptable salt thereof, for the manufacture of a medicament for the treatment and/or prevention of epilepsy, epileptogenesis, seizure disorders, convulsions, in particular, for the treatment of refractory seizures. Seizures can be classified as refractory when a patient fails to achieve seizure freedom for 12 months or more of state of the art treatment with two or more anti-epileptic drugs at maximal tolerated doses. The International League Against Epilepsy (ILAE) has defined drug resistant epilepsy as "failure of adequate trials of two tolerated and appropriately chosen and used AED schedules (whether as monotherapies or in combination) to achieve sustained seizure freedom".

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 1 to 2000 mg, preferably 1 to 1000 mg, more preferably 1 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manisfestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

A further aspect of the present invention relates to a pharmaceutical composition comprising an effective amount of a compound of formula (I) in combination with a pharmaceutically acceptable diluent or carrier.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

In accordance with the invention it has also been found that the compounds of formula (I) or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

For oral compositions, the daily dosage is in the range 1 mg to 2000 mg of compounds of formula (I). Preferably in the range 1 mg to 1000 mg of compounds of formula (I), most preferably 1 mg to 500 mg.

In compositions for parenteral administration, the quantity of compound of formula (I) present is at least 0.5% by weight and can be up to 33% by weight with respect to the total weight of the composition. For the preferred parenteral compositions, the dosage unit is in the range 1 mg to 2000 mg of compounds of formula (I).

The daily dose can fall within a wide range of dosage units of compound of formula (I) and is generally in the range 1 to 2000 mg, preferably 1 to 1000 mg. However, it should be understood that the specific doses can be adapted to particular cases depending on the individual requirements, at the physician's discretion.

The SV2 proteins binding compounds provided by this invention and labeled derivatives thereof may be useful as standards and reagents in determining the ability of tested compounds (e.g., a potential pharmaceutical) to bind to the SV2 proteins.

Labeled derivatives of SV2 proteins' ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A and SV2C, but including SV2B, to a putative agent and incubating the membranes or proteins or fragments and the agent with labelled compound of formula (I). The method further comprises determining if the binding of the compound of formula (I) to the protein is inhibited by the putative agent, thereby identifying binding partners for the protein. Thus, the screening assays enable the identification of new drugs or compounds that interact with SV2 proteins. The present invention also provides photoactivable ligands of SV2 proteins.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3$H, a fluorescent label, an enzyme, europium, biotin and other conventional labels for assays of this type.

Labelled compounds of formula (I) are useful in the methods as probes in assays to screen for new compounds or agents that bind to the SV2 proteins (SV2A, SV2B and SV2C). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the SV2 proteins (especially SV2A and SV2C), intact cells, cellular or membrane fragments containing SV2A or SV2C or the entire SV2 protein or a fragment thereof can be used. The agent or compound may be incubated with the cells, membranes, SV2 protein or fragment prior to, at the same time as, or after incubation with labelled levetiracetam or an analog or derivative thereof. Assays may be modified or prepared in any available format, including high-throughput screening (HTS) assays that monitor the binding of levetiracetam or the binding of derivatives or analogs thereof to SV2 proteins or fragments thereof. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 or of labelled levetiracetam, or derivatives or analogs thereof, to SV2 or a fragment of SV2 protein. The inhibition of complex formation may be detected by a variety of techniques such as filtration assays, Flashplates (Perkin Elmer), scintillation proximity assays (SPA, GE). For high-throughput screenings (HTS), scintillation proximity assay which uses microspheres coated with biological membranes or flashplates coated with biological membranes are powerful methods that do not require separation or washing steps.

A problem which can be faced when developing compounds for use in therapy is the capacity of certain compounds (perpetrator drugs), which could be co-administered together with the compounds of the present invention (victim drugs), to induce CYP450 enzymes, in particular CYP3A4/5. The induction of such enzymes by the perpetrator drugs may impact the exposure of the victim drug, when mainly metabolized by CYP450 enzymes and CYP3A4/5 in particular, thereby potentially altering their efficacy profile. It is therefore desirable to develop compounds with limited potential for metabolization by CYP3A4/5 enzymes.

The CYP3A4/5 contribution to the total metabolism of compounds according to the present invention has been evaluated by calculating the ratio between human hepatocytes clearances in absence and presence of a selective CYP3A4/5 inhibitor such as azamulin.

When tested in this assay according to the protocol described in the present patent application, compounds according to the accompanying Examples exhibit a fraction metabolized by CYP3A4/5 ($F_{m,CYP3A4/5}$) typically lower than 45%, therefore minimizing the risk for drug-drug interactions when coadministered with CYP450 inducers.

In addition, it may be beneficial that the compounds according to the present invention demonstrate low intrinsic clearances.

EXPERIMENTAL SECTION

Abbreviations/Recurrent Reagents

Ac: acetyl
ACN: Acetonitrile
Brine: Saturated aqueous sodium chloride solution
nBu: n-butyl
tBu: tert-butyl
Bz: benzoyl
CV: column volumes
DCM: Dichloromethane
DMF: N,N-Dimethylformamide
DMSO: Dimethylsulfoxide
Et: Ethyl
EtOH: Ethanol
$Et_2O$: Diethyl ether
EtOAc: Ethyl acetate
h: Hour
HPLC: High Pressure Liquid Chromatography
LC: Liquid Chromatography
LCMS: Liquid Chromatography Mass Spectrometry
MeOH: Methanol
min.: minutes
MTBE: methyl tert-butyl ether
NMR: Nuclear magnetic resonance
iPrOH: isopropanol
PTSA: p-toluenesulfonic acid
RT: room temperature
SFC: Supercritical Fluid Chromatography
THF: Tetrahydrofuran
TLC: Thin Layer Chromatography Analytical Methods All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v) in 6 min. with a hold at 100% B of 5 minutes. The flow rate is set at 8 mL/min during 6 min. then increased at 3 mL/min during 2 min. with a hold at 3 mL/min during 3 minutes. A split of $1/25$ is used just before API source. The chromatography is carried out at 45° C. The ammonium formate solution (pH~8.5) is prepared by dissolution of ammonium formate (630 mg) in water (1 L) and addition of ammonium hydroxide 30% (500 μL).

It will be apparent to the one skilled in the art that different retention times may be obtained for LC data if different analytical conditions are used.

Mass spectrometric measurements in LCMS mode are performed as follows:

For basic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an basic elution. The reverse phase separation is carried out at 45° C. on a Waters Acquity UPLC BEHC18 1.7 μm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 μL. Full flow in MS.

Basic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

Basic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 0 | 100 | 0.4 |
| 5.35 | 0 | 100 | 0.5 |
| 7.30 | 0 | 100 | 0.5 |

For acidic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an acidic elution. The reverse phase separation is carried out at 45° C. on a Waters Acquity UPLC HSS T3 1.8 μm (2.1×50 mm) column for acidic elution. Gradient elution is done with water/ACN/TFA (95/5/0.5 mL/L) (solvent A) and ACN (solvent B). Injection volume: 1 μL. Full flow in MS.

Acidic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 5 | 95 | 0.4 |
| 3.25 | 5 | 95 | 0.5 |
| 4 | 5 | 95 | 0.5 |

Acidic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.30 | 5 | 95 | 0.5 |

Crude materials could be purified by normal phase chromatography, (acidic or basic) reverse phase chromatography, chiral separation or recrystallization.

Normal reverse phase chromatography are performed using silica gel columns (100:200 mesh silica gel or Puriflash®-50SIHC-JP columns from Interchim).

Preparative Reverse Phase Chromatography are Performed as Follows:
  LCMS purification (Basic mode, LCMS prep) using a SQD or QM Waters triple quadrupole mass spectrometer is used for LCMS purification. This spectrometer is equipped with an ESI source and a Prep LC controller Waters quaternary pump with diode array detector (210 to 400 nm).

MS parameters: ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC parameters: The reverse phase separation is carried out at rt on a XBridge prep OBD C18 column (5 μm, 30×50 mm) (basic elution). Gradient elution is done with Water (solvent A), ACN (solvent B), Ammonium bicarbonate in water 8 g/L+500 μL/L NH₄OH 30% (solvent C) (pH~8.5). HPLC flow rate: 35 mL/min to 60 mL/min, injection volume: 1 mL. The splitting ratio is set at +/−1/6000 to MS.

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Products were generally dried under vacuum before final analyses and submission to biological testing.

NMR spectra are recorded on a BRUKER AVANCE III Ultrashield Nanobay 400 MHz NMR Spectrometer fitted with a Windows7 workstation running Bruker Topspin 3.2 software and a 5 mm BBI S1 with Z gradient probehead. Some NMR spectra are recorded on a BRUKER AVANCE III HD Ascend 500 MHz NMR Spectrometer fitted with a Windows7 workstation running Bruker Topspin 3.2 pl2 software and a 5 mm Prodigy BBO 500 S1 cryoprobe. The compounds are studied in $d_3$-chloroform or $d_6$-DMSO solution at a probe temperature of 300K. The instrument is locked on the deuterium signal of solvent used. Chemical shifts are given in ppm downfield from TMS (tetramethylsilane) taken as internal standard.

Compound names are generated by Accelrys Draw 4.0 or Biovia Draw 16.1

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Intermediates

A. Synthesis of 2-hydroxy-3-(2,2,2-trifluoroethyl)-2H-furan-5-one II

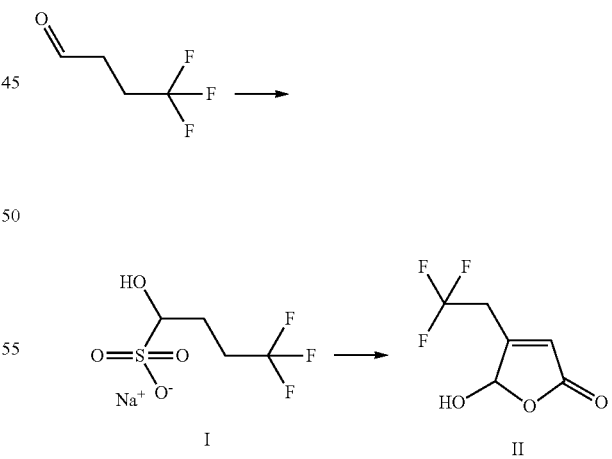

A.1. Synthesis of sodium; 4,4,4-trifluoro-1-hydroxy-butane-1-sulfonate I

To 4,4,4-trifluorobutyraldehyde (CAS: 406-87-1, 1.0 eq., 12.75 g, 101 mmol) was added at 0° C. sodium bisulfite (1.0 eq., 10.50 g, 101 mmol) in water (25 mL) and the mixture was stirred at 0° C. for 30 min. The precipitate was filtered and washed with cold methanol (500 mL) at 0° C. The obtained solid was dried under high vacuum at 40° C. for 16 h to give sodium; 4,4,4-trifluoro-1-hydroxy-butane-1-sulfonate I (15.4 g, 66.9 mmol) as a white solid which was used in the next step without any further purification.

Yield: 66%

$^1$H NMR (400 MHz, DMSO-d6): δ 5.60 (d, J=5.8 Hz, 1H), 3.92 (ddd, J=9.2, 5.7, 4.2 Hz, 1H), 2.35 (dddd, J=23.2, 11.6, 5.8, 3.4 Hz, 2H), 2.05-1.89 (m, 1H), 1.73 (dddd, J=13.9, 10.7, 8.6, 5.6 Hz, 1H).

A.2. Synthesis of 2-hydroxy-3-(2,2,2-trifluoroethyl)-2H-furan-5-one II

To a mixture of glyoxylic acid monohydrate (1.5 eq., 1.8 g, 19.5 mmol) and morpholine hydrochloride (1.5 eq., 2.4 g, 19.5 mmol) in a mixture of water (6 mL) and 1,4-dioxane (6 mL) at rt, was added sodium; 4,4,4-trifluoro-1-hydroxy-butane-1-sulfonate I (1.0 eq., 3.0 g, 13.0 mmol) and hydrochloric acid (2.0 eq., 2.2 mL, 26 mmol). The mixture was stirred for 20 h at 110° C. and then was cooled to rt. Water was added to the mixture and the aqueous layer was extracted with MTBE (3 times). The combined organic layers were washed with brine, dried over MgSO$_4$, filtered and evaporated until dryness to give 2-hydroxy-3-(2,2,2-trifluoroethyl)-2H-furan-5-one II (900 mg, 4.5 mmol, 90% estimated purity) which was used in the next step without any further purification.

Yield: 34%

LC/MS: [M–H]$^+$=180.9

$^1$H NMR (400 MHz, CDCl$_3$) δ 6.18 (s, 1H), 6.12 (s, 1H), 4.81 (s, 1H), 3.44-3.30 (m, 1H), 3.30-3.14 (m, 1H).

3-(2,2-difluoropropyl)-2-hydroxy-2H-furan-5-one II-A was prepared according to the same two steps procedure starting from 4,4-difluoropentanal (CAS: 1546331-97-8).

Yield: 40%

2-Hydroxy-3-(3,3,3-trifluoropropyl)-2H-furan-5-one III was prepared according to the same two-steps procedure starting from 5,5,5-trifluoropentanal (CAS: 250253-47-5).

Yield: 55% (1" step) and 73% (2$^d$ step).

2-Hydroxy-3-propyl-2H-furan-5-one III-A is commercially available (CAS: 78920-10-2) or may be prepared according to the same procedure starting from butyraldehyde.

3-(2,2-difluorocyclopropyl)-2-hydroxy-2H-furan-5-one III-B was prepared from 2-(2,2-difluorocyclopropyl)acetaldehyde according to a slightly modified procedure:

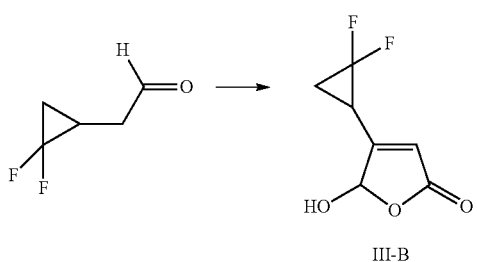

To a mixture of morpholine (1.1 eq., 1.07 g, 676.0 mmol, in heptane (55 mL) at 0° C. was added glyoxylic acid (0.95 eq., 965 mg, 614.5 mmol) and the mixture was stirred at 40° C. for 2 h. The mixture was then cooled to rt and 2-(2,2-difluorocyclopropyl)acetaldehyde (CAS: 1823961-57-4, 1.1 eq., 1.07 g, 676.0 mmol, was added and the mixture was stirred at 40° C. for 16 h. To the mixture cooled to 0° C. was added hydrochloric acid (1.75 eq., 1075.5 mmol, 12.2 mL, 36.5 mass %) and the mixture was stirred at room temperature for 2 h. Dichloromethane was then evaporated under vacuum at 25° C. and water was added to the obtained mixture. The aqueous layer was washed with heptane (3 times) and an aqueous saturated solution of Na$_2$CO$_3$ was added until pH=6-7. The aqueous layer was extracted with ethyl acetate (three times) and the combined organic layers were dried over MgSO$_4$, filtered and evaporated until dryness to give 3-(2,2-difluorocyclopropyl)-2-hydroxy-2H-furan-5-one III-B (1.5 g, 7.7 mmol, 90 mass %, estimated purity based on $^{19}$F-NMR) as a brown oil which was used as such in the next step.

Yield: 69%

LC/MS: [M–H]$^+$=175.00

$^1$H NMR (400 MHz, DMSO-d$_6$) δ 8.00 (q, J=2.9 Hz, 1H), 6.13-6.04 (m, 2H), 2.65 (dtd, J=43.0, 11.4, 7.8 Hz, 1H), 2.26-2.01 (m, 1H).

B. Synthesis of [2-(methoxymethyl)-6-methyl-imidazo[2,1-b][1,3,4]thiadiazol-5-yl]methanol V

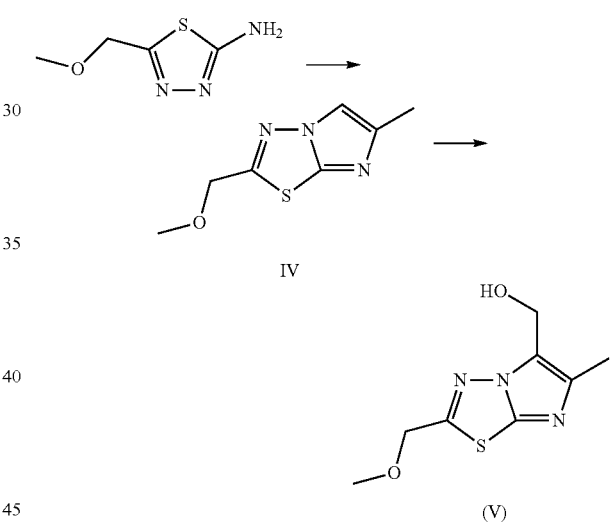

B.1 Synthesis of 2-(methoxymethyl)-6-methyl-imidazo[2,1-b][1,3,4]thiadiazole IV To a solution of 5-(methoxymethyl)-1,3,4-thiadiazol-2-amine (CAS: 15884-86-3, WO2011/047860, 1.0 eq., 7.0 g, 48.2 mmol) in DMF (95 mL), at 100° C., was added dropwise a solution of bromoacetone (1.0 eq., 4.2 mL, 46.2 mmol, 97% purity) in DMF (5 mL). The reaction mixture was stirred at 100° C. for 3 h. The reaction mixture was cooled to room temperature (RT) and the solvent was evaporated until dryness under high vacuum to give a brown oil. The crude was purified by flash chromatography Biotage Isolera Four (100 g KP-SNAP silica gel column in a gradient of 0% to 10% methanol in dichloromethane over 14CV) and the pure fractions were evaporated to dryness to give 2-(methoxymethyl)-6-methyl-imidazo[2,1-b][1,3,4]thiadiazole IV (5.0 g, 25.11 mmol) as a yellow/orange solid.

Yield: 52%

LC/MS: [M+H]$^+$=184.0

$^1$H NMR (400 MHz, DMSO-d$_6$): δ 8.53 (m, 1H), 4.76 (s, 2H), 3.40 (s, 3H), 2.25 (d, J=1.0 Hz, 3H).

B.2 Synthesis of [2-(methoxymethyl)-6-methyl-imidazo[2,1-b][1,3,4]thiadiazol-5-yl]methanol V In a sealed tube, 2-(methoxymethyl)-6-methyl-imidazo[2,1-b][1,3,4]thiadiazole IV (1.0 eq., 5.0 g, 25.1 mmol), paraformaldehyde (6.0 eq., 4.50 g, 150 mmol) and an aqueous solution of hydrochloric acid (4N) (2 equiv., 12.55 mL, 50.2 mmol) were mixed in 1,4-dioxane (12.5 mL). The mixture was stirred at 100° C. for 18 h, then the crude mixture was warmed to RT and an aqueous saturated solution of NaHCO$_3$ was added until pH=6-7. The aqueous layer was extracted with ethyl acetate (3 times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 5% methanol in dichloromethane over 12CV). The purest fractions were evaporated to dryness to give [2-(methoxymethyl)-6-methyl-imidazo[2,1-b][1,3,4]thiadiazol-5-yl]methanol V (4.0 g, 18.57 mmol) as a white solid.

Yield: 74%

LC/MS: [M+H]$^+$=214.0

$^1$H NMR (400 MHz, DMSO-d$_6$): δ 5.10 (t, J=5.4 Hz, 1H), 4.79 (s, 2H), 4.63 (d, J=5.4 Hz, 2H), 3.41 (s, 3H), 2.26 (s, 3H).

C. Synthesis of [6-(difluoromethyl)-2-(methoxymethyl)imidazo[2,1-b][1,3,4]thiadiazol-5-yl]methanol VII

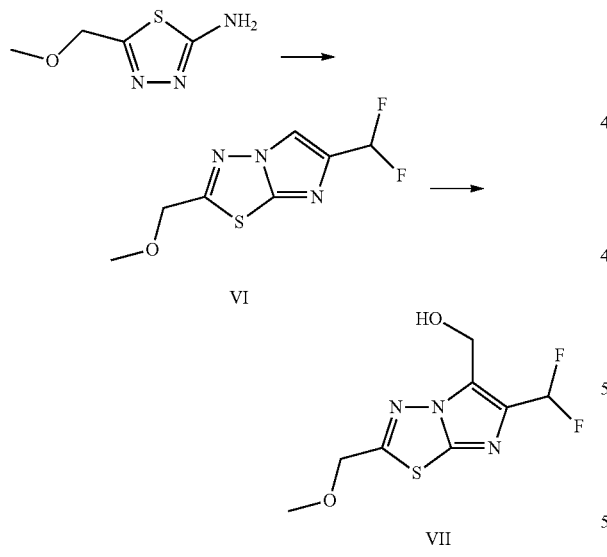

C.1. Synthesis of 6-(difluoromethyl)-2-(methoxymethyl)imidazo[2,1-b][1,3,4]thiadiazole VI To a solution of 5-(methoxymethyl)-1,3,4-thiadiazol-2-amine (CAS: 15884-86-3, 1.0 eq., 6.5 g, 45 mmol) in DMF (100 mL), at 100° C., was added dropwise a solution of 3-bromo-1,1-difluoro-propan-2-one (CAS: 883233-85-0, 1.05 eq., 8.1 g, 47 mmol) in DMF (5 mL). The reaction mixture was heated at 100° C. during 3 h and the completion was checked by LC/MS. A saturated aqueous solution of NaHCO$_3$ was added and the organic layer was extracted with ethyl acetate (three times). The combined organic layers were washed with water (five times), dried over MgSO$_4$, filtered and evaporated to dryness to give a brown solid (7.6 g). The crude was purified by flash chromatography Biotage Isolera Four (100 g KP-SNAP silica gel column in a gradient of 0% to 5% methanol in dichloromethane over 12 CV) and the pure fractions were combined and evaporated under high vacuum to give 6-(difluoromethyl)-2-(methoxymethyl)imidazo[2,1-b][1,3,4]thiadiazole VI (3.95 g, 17.8 mmol) as an orange solid.

Yield: 40%

LC/MS: [M+H]$^+$=220.2

$^1$H NMR (400 MHz, DMSO-d$_6$): δ 8.53 (t, J=2.2 Hz, 1H), 7.01 (t, J=54.6 Hz, 1H), 4.83 (s, 2H), 3.43 (s, 3H).

C.2. Synthesis of [6-(difluoromethyl)-2-(methoxymethyl)imidazo[2,1-b][1,3,4]thiadiazol-5-yl]methanol VII In a sealed tube, 6-(difluoromethyl)-2-(methoxymethyl)imidazo[2,1-b][1,3,4]thiadiazole VI (1.0 eq., 3.95 g, 18.0 mmol), paraformaldehyde (6.0 eq., 3.24 g, 108 mmol) and an aqueous solution of hydrochloric acid (2N) (0.9 equiv., 8.1 mL, 16.2 mmol) were mixed in 1,4-dioxane (8 mL). The mixture was stirred at 100° C. for 3.5 h and the reaction was checked by LC/MS. The crude mixture was warmed to RT and an aqueous saturated solution of NaHCO$_3$ was added until pH=6-7. The aqueous layer was extracted with ethyl acetate (three times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 10% methanol in dichloromethane over 15 CV) to give a yellow oil (3 g) which was purified a second time by reverse phase HPLC (KROMA-SIL-Eternity XT C$_{18}$ 10 μm/ACN/H$_2$O/NH$_4$OH gradient from 20/80/0.1 to 50/50/0.1). The purest fractions were evaporated to dryness to give [6-(difluoromethyl)-2-(methoxymethyl)imidazo[2,1-b][1,3,4]thiadiazol-5-yl]methanol VII (2 g, 8.02 mmol) as a white solid.

Yield: 45%

LC/MS: [M+H]$^+$=250.2

$^1$H NMR (400 MHz, DMSO-d$_6$): δ 7.11 (t, J=53.6 Hz, 1H), 5.47 (t, J=5.4 Hz, 1H), 4.84 (s, 2H), 4.79 (d, J=5.5, Hz, 2H), 3.44 (d, J=0.9 Hz, 3H).

D. [6-(1-fluorocyclopropyl)-2-(methoxymethyl)imidazo[2,1-b][1,3,4]thiadiazol-5-yl]methanol VII-A

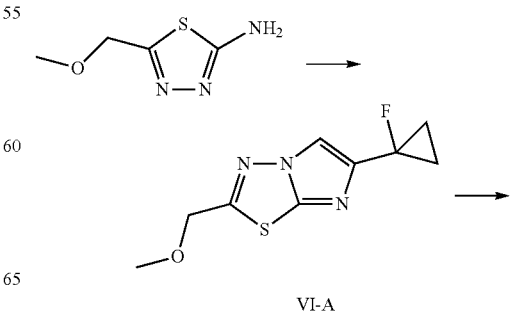

25

-continued

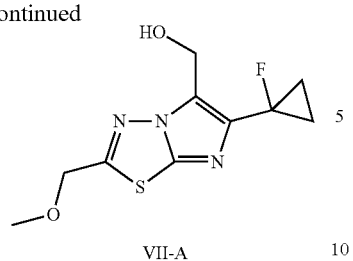

VII-A

D.1. Synthesis of 6-(1-fluorocyclopropyl)-2-(methoxymethyl)imidazo[2,1-b][1,3,4]thiadiazole VI-A To a solution of 5-(methoxymethyl)-1,3,4-thiadiazol-2-amine (1 eq., 2.0 g, 13.7 mmol) in DMF (30 mL) at 10° C. was added dropwise a solution of 2-chloro-1-(1-fluorocyclopropyl)ethanone (CAS: 151697-21-1, 1.05 eq., 1.97 g, 14.4 mmol) in DMF (2 mL). The reaction mixture was heated at 100° C. during 2 h 30, then a saturated aqueous solution of NaHCO$_3$ was added and the aqueous layer was extracted with ethyl acetate (three times). The combined organic layers were washed with water (5 times), dried over MgSO$_4$, filtered and evaporated to dryness to give a brown oil. The crude was purified by reverse phase preparative HPLC Gilson (YMC Triart C18 80×204-10 μm-500 g-gradient ACN/H$_2$O 40/60 to 95/05) to give 6-(1-fluorocyclopropyl)-2-(methoxymethyl)imidazo[2,1-b][1,3,4]thiadiazole VI-A (1.16 g, 5.10 mmol) as a beige solid.

Yield: 37%

LC/MS: [M+H]$^+$=228.00

$^1$H NMR (400 MHz, DMSO-d$_6$) δ 8.24 (d, J=0.9 Hz, 1H), 4.79 (s, 2H), 3.41 (s, 3H), 1.50-1.31 (m, 2H), 1.13 (dt, J=8.4, 1.8 Hz, 2H).

D.2. Synthesis of [6-(1-fluorocyclopropyl)-2-(methoxymethyl)imidazo[2,1-b][1,3,4]thiadiazol-5-yl]methanol VII-A To a solution of 6-(1-fluorocyclopropyl)-2-(methoxymethyl)imidazo[2,1-b][1,3,4]thiadiazole (VI-A, 1 eq., 395 mg, 1.74 mmol) and paraformaldehyde (6 eq., 312.8 mg, 10.43 mmol) in 1,4-dioxane (1.7 mL) was added hydrochloric acid (4 eq., 1.82 g, 6.95 mmol, 4 mol/L) and the mixture was stirred at 100° C. during 1 h. A saturated aqueous solution of NaHCO$_3$ was added and the aqueous layer was extracted with ethyl acetate (three times). The combined organic layers were dried over MgSO$_4$, filtered and evaporated to dryness to give a brown oil which was purified by SFC (PREP 600, Column P4VP 50×174-5 μm-200 g with co-solvent MeOH 5%) to give [6-(1-fluorocyclopropyl)-2-(methoxymethyl)imidazo[2,1-b][1,3,4]thiadiazol-5-yl]methanol VII-A (250 mg, 0.92 mmol) as a beige solid.

Yield: 53%

LC/MS: [M+H]$^+$=258.02

26

EXAMPLES

Synthesis of 1-[[2-(methoxymethyl)-6-(trifluoromethyl)imidazo[2,1-b][1,3,4]thiadiazol-5-yl]methyl]-3-propyl-2H-pyrrol-5-one 1

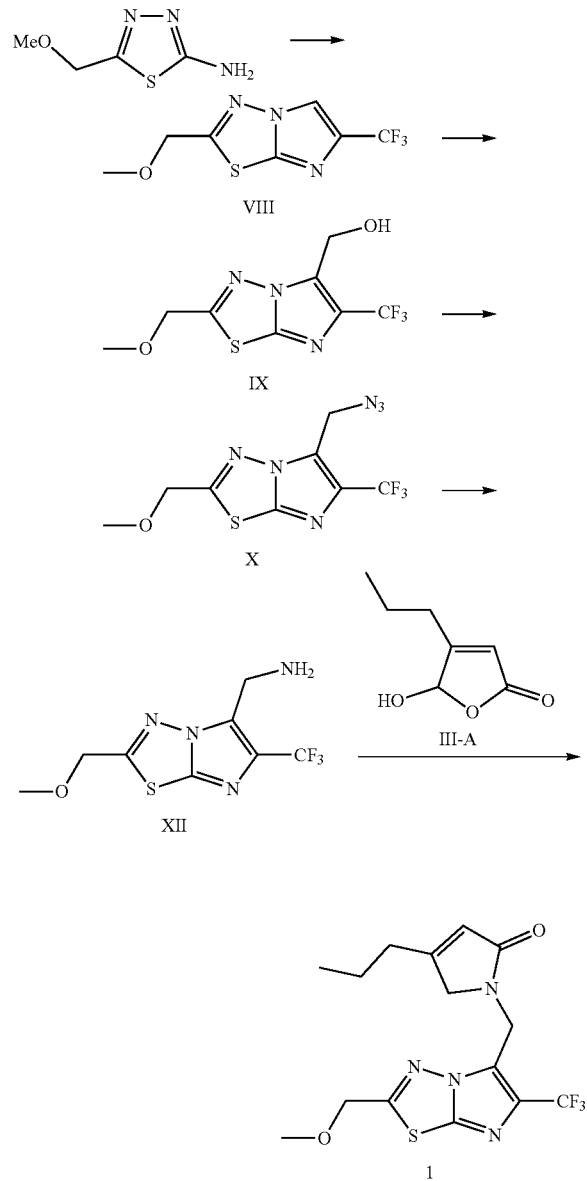

1.1 Synthesis of 2-(methoxymethyl)-6-(trifluoromethyl)imidazo[2,1-b][1,3,4]thiadiazole VIII 3-Bromo-1,1,1-trifluoroacetone (CAS: 431-35-6, 478 g, 2.5 mol, 1.05 eq) is added on a suspension of 5-(methoxymethyl)-1,3,4-thiadiazol-2-amine (CAS: 15884-86-33, 46 g, 2.4 mol, 1 eq) in 1,2-dimethoxyethane (6 l) at 20° C. The reaction mixture is heated to 80° C. until maximum conversion (<24 h). Water (4 l) is added to the reaction mixture at 32° C. and the expected compound crystallized out of the reaction mixture. The crystalline suspension is cooled to 10° C. to complete the crystallization process, filtered and the crystalline precipitate is washed with water (1.5 l) to afford 266 g of pure 2-(methoxymethyl)-6-(trifluoromethyl)imidazo[2,1-b][1,3,4]thiadiazole VIII.

Yield: 47%.
LC-MS (MH$^+$): 238.

1.2 Synthesis of [2-(methoxymethyl)-6-(trifluoromethyl)imidazo[2,1-b][1,3,4]thiadiazol-5-yl]methanol IX 2-(methoxymethyl)-6-(trifluoromethyl)imidazo[2,1-b][1,3,4]thiadiazole VIII (10 g, 42.16 mmol, 1 eq), formaldehyde (16 g, 421.6 mmol, 10 eq) and hydrochloric acid (37%, 8.2 ml, 2 eq) are diluted in sulfolane (250 ml). The reaction mixture is heated at 110° C. overnight. Water (500 ml) is added and the mixture is heated at 50° C. for 2 h. The solvent is then removed under reduced pressure. The residue is purified by chromatography over silicagel (gradient; eluent: CH$_2$Cl$_2$/MeOH/NH$_4$OH from 100/0/0 to 99/1/0.1) to afford 6.5 g of [2-(methoxymethyl)-6-(trifluoromethyl)imidazo[2,1-b][1,3,4]thiadiazol-5-yl]methanol IX as a yellow solid.

Yield: 58%.
LC-MS (MH$^+$): 268.

1.3 Synthesis of 5-(azidomethyl)-2-(methoxymethyl)-6-(trifluoromethyl)imidazo[2,1-b][1,3,4]thiadiazole X N,N-Diisopropylethylamine (3.22 g, 24.88 mmol, 5 eq) and methanesulfonyl chloride (0.855 g, 7.47 mmol, 1.5 eq) are successively and slowly added at 0° C. to a solution of [2-(methoxymethyl)-6-(trifluoromethyl)imidazo[2,1-b][1,3,4]thiadiazol-5-yl]methanol IX (1.33 g, 4.98 mmol, 1 eq) in dichloromethane (30 ml). Sodium azide (0.485 g, 7.47 mmol, 1.5 eq) in suspension in DMF (5 ml) is added at 0° C., then warmed up to room temperature and the reaction mixture is stirred overnight. After hydrolysis (H$_2$O) and extraction with diethylether, the combined organic layers are dried over MgSO$_4$, filtered and evaporated under reduced pressure to afford 1.45 g of 5-(azidomethyl)-2-(methoxymethyl)-6-(trifluoromethyl)imidazo[2,1-b][1,3,4]thiadiazole X.

Yield: 100%.
LC-MS (MH$^+$): 293.

5-(azidomethyl)-2-(methoxymethyl)-6-methyl-imidazo[2,1-b][1,3,4]thiadiazole XI is prepared according to the same procedure starting from [2-(methoxymethyl)-6-methyl-imidazo[2,1-b][1,3,4]thiadiazol-5-yl]methanol V.

Yield: 62%
LC-MS (MH$^+$): 239

1.4 Synthesis of 1-[2-(methoxymethyl)-6-(trifluoromethyl)imidazo[2,1-b][1,3,4]thiadiazol-5-yl]methanamine XII Triphenylphosphine (1.31 g, 4.98 mmol, 1 eq) is added at room temperature to a suspension of 5-(azidomethyl)-2-(methoxymethyl)-6-(trifluoromethyl)imidazo[2,1-b][1,3,4]thiadiazole X (1.45 g, 4.98 mmol, 1 eq) in THF/H$_2$O (18 ml/2 ml). The reaction mixture is stirred at room temperature for 60 h. The solvent is evaporated under reduced pressure, water is added to the residue, the solution is acidified to pH 2 with aqueous 5N HCl, then extracted with Et$_2$O (1×50 ml). The aqueous layer is basified (pH 8) by addition of a Na$_2$CO$_3$ aqueous solution, and extracted with dichloromethane (2×50 ml), the cumulated organics layers are dried over MgSO$_4$, filtered and evaporated under reduced pressure to afford 1.16 g of 1-[2-(methoxymethyl)-6-(trifluoromethyl)imidazo[2,1-b][1,3,4]thiadiazol-5-yl]methanamine XII.

Yield: 88%.
LC-MS (MH$^+$): 267.

[2-(methoxymethyl)-6-methyl-imidazo[2,1-b][1,3,4]thiadiazol-5-yl]methanamine XIII is prepared according to the same procedure starting from 5-(azidomethyl)-2-(methoxymethyl)-6-methyl-imidazo[2,1-b][1,3,4]thiadiazole XI. Purification of the crude mixture was performed by reverse phase preparative HPLC (KROMASIL-Eternity XT C$_{18}$ 10 μm/ACN/H$_2$O/NH$_4$OH gradient from 20/80/0.1 to 95/5/0.1)

Yield: 74%.
LC-MS (MH$^+$): 213
$^1$H NMR (400 MHz, DMSO-d$_6$): δ 4.79 (s, 2H), 3.88 (s, 2H), 3.41 (s, 3H), 2.24 (s, 3H).

1.5 Synthesis of 1-[[2-(methoxymethyl)-6-(trifluoromethyl)imidazo[2,1-b][1,3,4]thiadiazol-5-yl]methyl]-3-propyl-2H-pyrrol-5-one 1

2-Hydroxy-3-propyl-2H-furan-5-one III-A (CAS: 78920-10-2, 160.8 mg, 1.127 mmol, 1 eq.) and 1-[2-(methoxymethyl)-6-(trifluoromethyl)imidazo[2,1-b][1,3,4]thiadiazol-5-yl]methanamine XII (300 mg, 1.127 mmol, 1 eq.) are dissolved in dry methanol (3 ml) and the mixture is stirred at room temperature for 3 h 30, then cooled at 0° C. Sodium borohydride (42.8 mg, 1.127 mmol, 1 eq.) is added and the reaction is stirred at 0° C. for 1 h. 0.5 ml of acetic acid are added and the mixture is stirred at room temperature overnight. The solvent is evaporated under reduced pressure, water and dichloromethane are added to the residue and the mixture is extracted three times with dichloromethane. Combined organic layers are dried over MgSO$_4$, filtered and evaporated under reduced pressure. The residue (327 mg) is purified by chromatography over silicagel (CH$_2$Cl$_2$/MeOH/NH$_4$OH 99/1/0.1) and further recrystallized from heptane/diethylether (80/20) to afford 127.6 mg of pure 1-[[2-(methoxymethyl)-6-(trifluoromethyl)imidazo[2,1-b][1,3,4]thiadiazol-5-yl]methyl]-3-propyl-2H-pyrrol-5-one 1.

Yield: 30%.
LC-MS (MH$^+$): 375
$^1$H NMR (400 MHz, DMSO-d$_6$): δ 5.71 (s, 1H), 4.82 (s, 2H), 4.75 (s, 2H), 3.80 (s, 2H), 3.35 (s, 3H), 2.19 (t, J=7.5 Hz, 2H), 1.40 (m, 2H), 0.79 (t, J=7.3 Hz, 3H) 1-[[2-(methoxymethyl)-6-(trifluoromethyl)imidazo[2,1-b][1,3,4]thiadiazol-5-yl]methyl]-3-(2,2,2-trifluoroethyl)-2H-pyrrol-5-one 2 is prepared according to the same procedure starting from 2-hydroxy-3-(2,2,2-trifluoroethyl)-2H-furan-5-one II.

Yield: 30%
LC-MS (MH$^+$): 415
$^1$H NMR (400 MHz, DMSO-d$_6$): δ 6.09 (s, 1H), 4.95 (s, 2H), 4.82 (s, 2H), 4.00 (s, 2H), 3.55 (q, 2H), 3.43 (s, 3H).
1-[[2-(methoxymethyl)-6-(trifluoromethyl)imidazo[2,1-b][1,3,4]thiadiazol-5-yl]methyl]-3-(3,3,3-trifluoropropyl)-2H-pyrrol-5-one 3 is prepared according to the same procedure starting from 2-hydroxy-3-(3,3,3-trifluoropropyl)-2H-furan-5-one III.

Yield: 34%
LC-MS (MH$^+$): 429
$^1$H NMR (400 MHz, DMSO-d$_6$): δ 5.95 (s, 1H), 4.92 (s, 2H), 4.82 (s, 2H), 3.94 (s, 2H), 3.45 (s, 3H), 2.45 (m, 4H).

1-[[2-(methoxymethyl)-6-methyl-imidazo[2,1-b][1,3,4]thiadiazol-5-yl]methyl]-3-propyl-2H-pyrrol-5-one 4 is prepared according to the same procedure starting from [2-(methoxymethyl)-6-methyl-imidazo[2,1-b][1,3,4]thiadiazol-5-yl]methanamine XIII and 2-hydroxy-3-propyl-2H-furan-5-one III-A (CAS: 78920-10-2).

Yield: 30%

LC/MS: [M+H]$^+$=321

$^1$H NMR (400 MHz, DMSO-d$_6$) δ 5.78 (s, 1H), 4.77 (s, 2H), 4.72 (s, 2H), 3.87 (s, 2H), 3.40 (s, 3H), 2.27 (d, J=4.1 Hz, 5H), 1.48 (h, J=7.4 Hz, 2H), 0.87 (t, J=7.3 Hz, 3H).

Synthesis of 1-[[2-(methoxymethyl)-6-(trifluoromethyl)imidazo[2,1-b][1,3,4]thiadiazol-5-yl]methyl]-3-propyl-2H-pyrrol-5-one 5

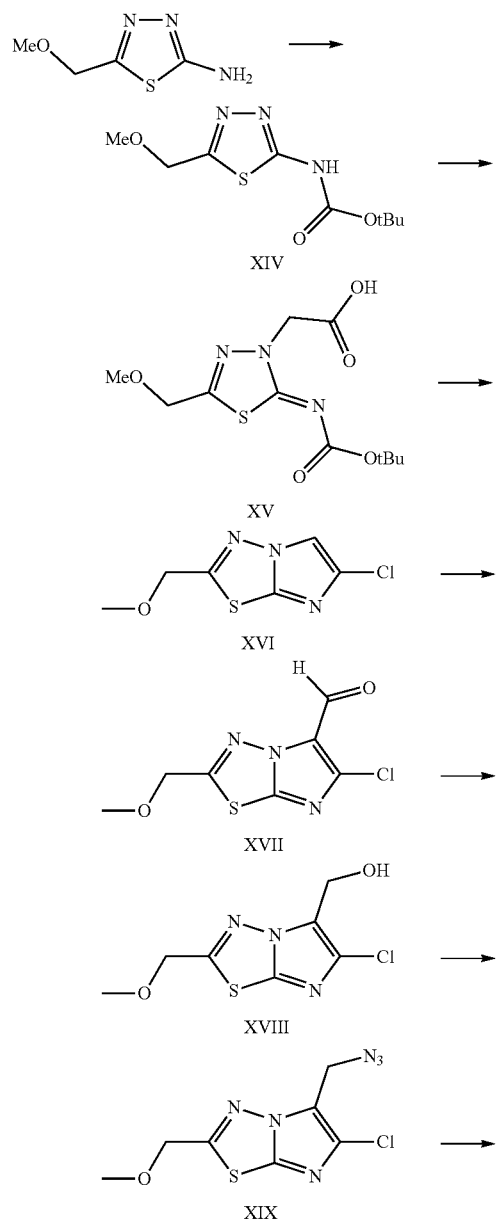

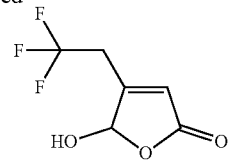

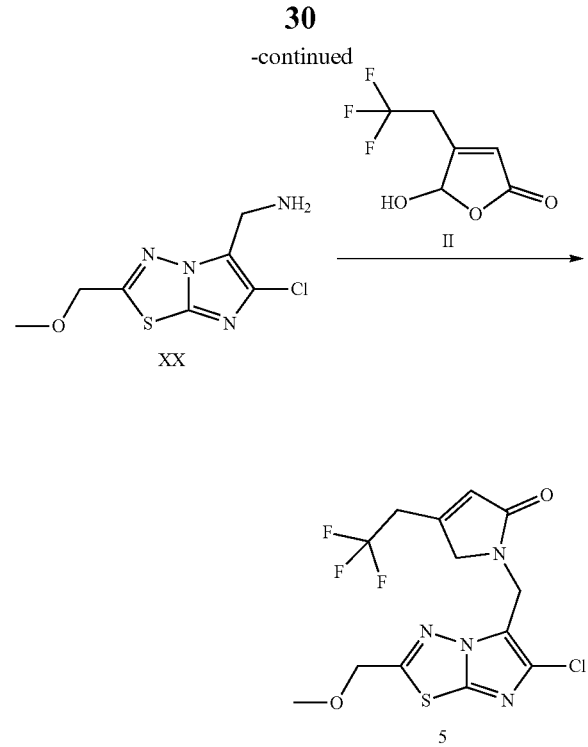

2.1 Synthesis of tert-butyl[5-(methoxymethyl)-1,3,4-thiadiazol-2-yl]carbamate XIV To a suspension of 5-(methoxymethyl)-1,3,4-thiadiazol-2-amine (CAS: 15884-86-33, 100 g, 0.69 mol, 1 eq) in dichloromethane (1 l) at room temperature are added, successively and each in one portion, di-tert-butyl dicarbonate (132 g, 0.76 mol, 1.1 eq) and N,N-dimethylamino-pyridine (8.35 g, 0.069 mol, 0.1 eq). After overnight stirring at room temperature, the reaction mixture is washed with 1N HCl (pH 5) to remove N,N-dimethylaminopyridine. The solvent is removed under reduced pressure and the residue is recrystallized from di-isopropyl ether to afford 148.9 g of pure tert-butyl[5-(methoxymethyl)-1,3,4-thiadiazol-2-yl]carbamate XIV.

Yield: 88%.

LC-MS (MH$^+$): 246.

2.2 Synthesis of {2-[(tert-butoxycarbonyl)imino]-5-(methoxymethyl)-1,3,4-thiadiazol-3(2H)-yl}acetic acid XV Iodoacetic acid (409.3 g, 2.2 mol, 1.5 eq) is added in one portion to a solution of tert-butyl[5-(methoxymethyl)-1,3,4-thiadiazol-2-yl]carbamate XIV (360 g, 1.47 mol, 1 eq) in tetrahydrofurane (3 l) at room temperature. Sodium hydride (52.8 g, 2.2 mol, 1.5 eq) is then added portionwise, in 30 minutes, at room temperature. The reaction mixture is heated at 60° C. overnight, and the solvent is evaporated under reduced pressure. Water is added to the residue, the solution is acidified to pH=2 with aqueous 6N HCl, then extracted with CH$_2$Cl$_2$. The organic layer is washed with 10% aqueous sodium thiosulfate and evaporated to dryness to afford 455.7 g of {2-[(tert-butoxy-carbonyl)imino]-5-

(methoxymethyl)-1,3,4-thiadiazol-3(2H)-yl}acetic acid XV which is used directly in the next step without any further purification.

Yield: 90%.

LC-MS (MH$^+$): 304.

2.3 Synthesis of 6-chloro-2-(methoxymethyl)imidazo[2,1-b][1,3,4]thiadiazole XVI To {2-[(tert-butoxycarbonyl)imino]-5-(methoxymethyl)-1,3,4-thiadiazol-3(2H)-yl}acetic acid XV (418 g, 1.38 mol, 1 eq) in acetonitrile (2.5 l) at room temperature, are successively and slowly added triethyl amine (278.9 g, 2.76 mol, 2 eq), then phosphorous oxychloride (633.9 g, 4.13 mol, 3 eq). The reaction mixture is heated at 80° C. for one hour. After reaction completion, water (2.2 l) is slowly and carefully added at 50° C. The reaction mixture is extracted with dichloromethane (2×1.2 l), the combined organic layers are washed by a NaOH/NaCl aqueous solution (1.4 l of saturated NaCl solution+400 ml 2N NaOH), dried over MgSO$_4$, filtered and condensed under reduced pressure. The residue is recrystallized from acetonitrile/water (1/1) to afford 99.8 g of pure 6-chloro-2-(methoxymethyl)imidazo[2,1-b][1,3,4]thiadiazole XVI.

Yield: 36%.

LC-MS (MH$^+$): 204/206.

2.4 Synthesis of 6-chloro-2-(methoxymethyl)imidazo[2,1-b][1,3,4]thiadiazole-5-carbaldehyde XVII Phosphorus oxychloride (2.75 ml, 3 eq) is added very slowly to dimethyl formamide (5 ml) cooled at 0° C. The temperature rises to 50° C. The reaction mixture is heated at 60° C., then 6-chloro-2-(methoxymethyl)imidazo[2,1-b][1,3,4]thiadiazole XVI (2 g, 9.82 mmol, 1 eq) is added portionwise for 2.5 h. The reaction mixture is poured on an ice/water mixture. The precipitate is filtered and washed with water. The residue is dried overnight at 40° C. under reduced pressure to afford 1.8 g of 6-chloro-2-(methoxymethyl)imidazo[2,1-b][1,3,4]thiadiazole-5-carbaldehyde XVII as a solid.

Yield: 79%.

LC-MS (MH$^+$): 232/234.

2.5 Synthesis of [6-chloro-2-(methoxymethyl)imidazo[2,1-b][1,3,4]thiadiazol-5-yl]-methanol XVIII 6-chloro-2-(methoxymethyl)imidazo[2,1-b][1,3,4]thiadiazole-5-carbaldehyde XVII (2.97 g, 12.94 mmol, 1 eq) is dissolved in ethanol (80 ml), cooled at 0° C. and sodium borohydride (578 mg, 15.53 mmol, 1.2 eq) is added portionwise at 0° C. The reaction mixture is stirred overnight at room temperature, then cooled at 0° C. and a saturated NH$_4$Cl aqueous solution (100 ml) is added. The organic solvent is evaporated under reduced pressure and the precipitate is filtered, dried under vacuum at 20° C. to afford 1.99 g of [6-chloro-2-(methoxymethyl)imidazo[2,1-b][1,3,4]thiadiazol-5-yl]methanol XVIII.

Yield: 66%.

LC-MS (MH$^+$): 234/236.

2.6 Synthesis of 5-(azidomethyl)-6-chloro-2-(methoxymethyl)imidazo[2,1-b][1,3,4]thiadiazole XIX N,N-Diisopropylethylamine (10.7 mmol, 5 eq) and methanesulfonyl chloride (0.368 g, 3.21 mmol, 1.5 eq) are successively and slowly added at 0° C. to a solution of [6-chloro-2-(methoxymethyl)imidazo[2,1-b][1,3,4]thiadiazol-5-yl]methanol XVIII (0.5 g, 2.14 mmol, 1 eq) in dichloromethane (12.5 ml). Sodium azide (0.209 g, 3.21 mmol, 1.5 eq) in suspension in DMF (5 ml) is added at 0° C., then warmed up to room temperature and the reaction mixture is stirred overnight. After hydrolysis (H$_2$O) and extraction with diethylether, the combined organic layers are dried over MgSO$_4$, filtered and evaporated under reduced pressure to afford 434 mg of 5-(azidomethyl)-6-chloro-2-(methoxymethyl)imidazo[2,1-b][1,3,4]thiadiazole XIX which is used in the next step without further purification.

Yield: 78%

LC-MS (MH$^+$): 259/261.

2.7 Synthesis of [6-chloro-2-(methoxymethyl)imidazo[2,1-b][1,3,4]thiadiazol-5-yl]methanamine XX Triphenylphosphine (0.438 g, 1.68 mmol, 1 eq) is added at room temperature to a suspension of 5-(azidomethyl)-6-chloro-2-(methoxymethyl)imidazo[2,1-b][1,3,4]thiadiazole XIX (0.434 g, 1.68 mmol, 1 eq) in THF/H$_2$O (7.5 ml/0.75 ml). The reaction mixture is stirred at room temperature for 15 h. The solvent is evaporated under reduced pressure, water is added to the residue, the solution is acidified to pH 2 with aqueous 5N HCl, then extracted with Et$_2$O (1×50 ml). The aqueous layer is basified (pH 8) by addition of a Na$_2$CO$_3$ aqueous solution, and extracted with dichloromethane (2×50 ml), the cumulated organics layers are dried over MgSO$_4$, filtered and evaporated under reduced pressure to afford 0.34 g of 1-[2-(methoxymethyl)-6-(trifluoromethyl)imidazo[2,1-b][1,3,4]thiadiazol-5-yl]methanamine XX.

Yield: 87%.

LC-MS (MH$^+$): 233/235.

2.8 Synthesis of 1-[[6-chloro-2-(methoxymethyl)imidazo[2,1-b][1,3,4]thiadiazol-5-yl]methyl]-3-(2,2,2-trifluoroethyl)-2H-pyrrol-5-one 5

2-hydroxy-3-(2,2,2-trifluoroethyl)-2H-furan-5-one (340 mg, 1.87 mmol, 1 eq.) and 1-[2-(methoxymethyl)-6-(trifluoromethyl)imidazo[2,1-b][1,3,4]thiadiazol-5-yl]methanamine XX (434 mg, 1.87 mmol, 1 eq.) are dissolved in dry methanol (10 ml) and the mixture is stirred overnight at room temperature, then cooled at 0° C. Sodium borohydride (77 mg, 2.03 mmol, 1.08 eq.) is added and the reaction is stirred at 0° C. for 1 h. 1 ml of acetic acid are added and the mixture is stirred 1 h at room temperature. The solvent is evaporated under reduced pressure, water and dichloromethane are added to the residue and the mixture is extracted three times with dichloromethane. Combined organic layers are dried over MgSO$_4$, filtered and evaporated under reduced pressure. The residue (800 mg) is purified by flash chromatography over silicagel (CH$_2$Cl$_2$/MeOH 98/2) and further recrystallized from acetonitrile to afford 119 mg of pure 1-[[6-chloro-2-(methoxymethyl)imidazo[2,1-b][1,3,4]thiadiazol-5-yl]methyl]-3-(2,2,2-trifluoroethyl)-2H-pyrrol-5-one 5.

Yield: 16%.

LC-MS (MH$^+$): 381/383

$^1$H NMR (400 MHz, DMSO-d$_6$): δ 6.08 (s, 1H), 4.80 (s, 4H), 4.02 (s, 2H), 3.55 (q, 2H), 3.40 (s, 3H).

1-[[6-chloro-2-(methoxymethyl)imidazo[2,1-b][1,3,4]thiadiazol-5-yl]methyl]-3-propyl-2H-pyrrol-5-one 6 is prepared according to the same procedure starting from 2-hydroxy-3-propyl-2H-furan-5-one III-A (CAS: 78920-10-2).

Yield: 50%.

LC-MS (MH$^+$): 341/343

$^1$H NMR (400 MHz, DMSO-d$_6$): δ 5.78 (s, 1H), 4.83 (s, 2H), 4.77 (s, 2H), 3.91 (s, 2H), 3.43 (s, 3H), 2.28 (dd, 2H), 1.48 (m, 2H), 0.87 (t, 3H).

1-[[6-chloro-2-(methoxymethyl)imidazo[2,1-b][1,3,4]thiadiazol-5-yl]methyl]-3-(3,3,3-trifluoropropyl)-2H-pyrrol-5-one 7 is prepared according to the same procedure starting from 2-hydroxy-3-(3,3,3-trifluoropropyl)-2H-furan-5-one III.

Yield: 24%.

LC-MS (MH$^+$): 395/397

$^1$H NMR (400 MHz, DMSO-d$_6$): δ 5.94 (s, 1H), 4.80 (s, 2H), 4.75 (s, 2H), 3.96 (s, 2H), 3.43 (q, 2H), 3.56 (s, 3H).

Synthesis of 1-[[6-(difluoromethyl)-2-(methoxymethyl)imidazo[2,1-b][1,3,4]thiadiazol-5-yl]methyl]-3-propyl-2H-pyrrol-5-one 8

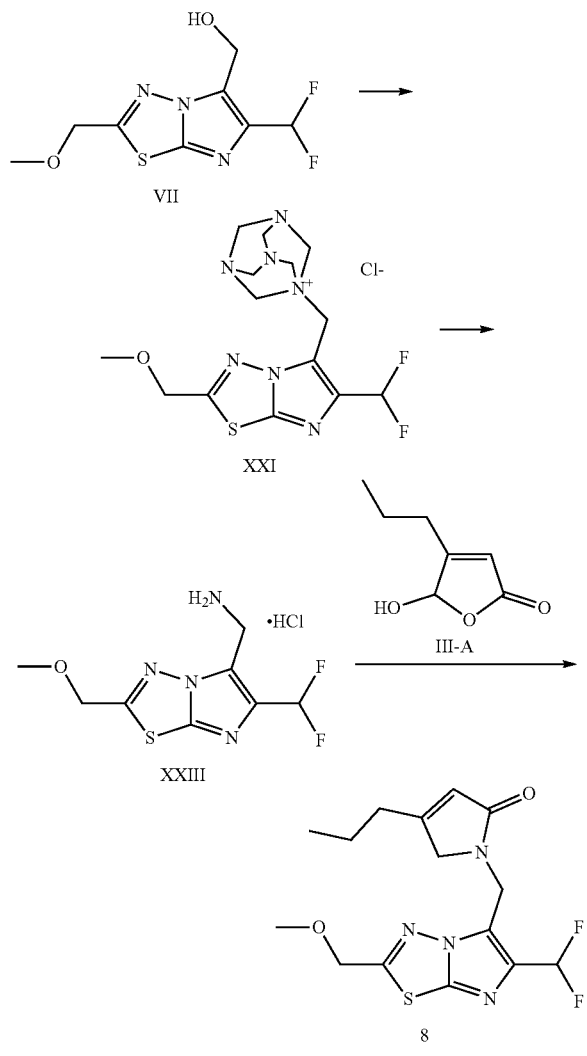

3.1. Synthesis of hexamethylenetetramine salt XXI

To a mixture of [6-(difluoromethyl)-2-(methoxymethyl)imidazo[2,1-b][1,3,4]thiadiazol-5-yl]methanol VII (1.0 eq., 500 mg, 2.0 mmol) in dichloromethane (10 mL) at 0° C. was added thionyl chloride (1.2 eq., 287 mg, 2.4 mmol). The reaction was stirred at 0° C. for 10 min and then at rt for 1 h. The crude mixture was evaporated to dryness and the obtained glue was solubilized in dichloromethane (10 mL) before addition of hexamethylenetetramine (3.0 eq., 852 mg, 6.0 mmol). The reaction was then stirred at 35° C. for 2 h, cooled down to 0° C., filtered and washed with cooled dichloromethane, to give XXI (900 mg, 1.87 mmol, 85% estimated purity) as a beige solid which was used in the next step without any further purification.

Yield: 93%

LC/MS: [M+H]$^+$=372

Hexamethylenetetramine salt XXII is prepared according to the same procedure starting from starting from [2-(methoxymethyl)-6-methyl-imidazo[2,1-b][1,3,4]thiadiazol-5-yl]methanol V.

Yield: quantitative.

LC-MS (MH$^+$): 336

3.2. Synthesis of [6-(difluoromethyl)-2-(methoxymethyl)imidazo[2,1-b][1,3,4]thiadiazol-5-yl]methanamine hydrochloride XXIII To a mixture of hexamethylenetetramine salt XXI (1.0 eq., 818 mg, 1.70 mmol, 85% estimated purity) in methanol (5 mL) was added hydrochloric acid (4.5 eq., 914 mg, 9.0 mmol) at room temperature. The reaction was stirred at 45° C. for 1 h and the mixture was filtered. The obtained filtrate was then evaporated to dryness to give [6-(difluoromethyl)-2-(methoxymethyl)imidazo[2,1-b][1,3,4]thiadiazol-5-yl]methanamine; hydrochloride XXIII (900 mg, 1.74 mmol, 55% estimated purity) as an impure beige solid which was used in the next step without further purification.

Yield: quantitative

LC/MS: [M+H]$^+$=249

[2-(methoxymethyl)-6-methyl-imidazo[2,1-b][1,3,4]thiadiazol-5-yl]methanamine hydrochloride XXIV is prepared according to the same procedure starting from hexamethylenetetramine salt XXII.

Yield: 55%

LC/MS: [M+H]$^+$=213

3.3. Synthesis of 1-[[6-(difluoromethyl)-2-(methoxymethyl)imidazo[2,1-b][1,3,4]thiadiazol-5-yl]methyl]-3-propyl-2H-pyrrol-5-one 8

A mixture of [6-(difluoromethyl)-2-(methoxymethyl)imidazo[2,1-b][1,3,4]thiadiazol-5-yl]methanamine hydrochloride XXIII (1 eq., 210 mg, 0.48 mmol, 65% estimated purity), 2-hydroxy-3-propyl-2H-furan-5-one III-A (3.0 eq., 241 mg, 1.44 mmol, 85% $^1$H NMR purity) and sodium hydroxide (2.0 eq., 39 mg, 0.96 mmol) in methanol (2 mL) was stirred at rt for 2 h. To the solution cooled down to 0° C. was added sodium borohydride (2 eq., 36 mg, 0.96 mmol) and the mixture was stirred at 0° C. for 1 h. Acetic acid (5.0 eq., 144 mg, 2.4 mmol) was then added and the mixture was stirred at rt for 3 h. The crude mixture was evaporated to dryness to give an orange glue which was purified by reverse phase preparative HPLC (KROMASIL-Eternity XT C$_{18}$ 10 μm/ACN/H$_2$O/NH$_4$OH gradient from 30/70/0.1 to 60/40/0.1), to give 1-[[6-(difluoromethyl)-2-(methoxymethyl)imidazo[2,1-b][1,3,4]thiadiazol-5-yl]methyl]-3-propyl-2H-pyrrol-5-one 8 (42 mg, 0.12 mmol) as a beige solid.

Yield: 24%

LC/MS: [M+H]$^+$=357

$^1$H NMR (400 MHz, CDCl$_3$) δ 6.88 (t, J=54.5 Hz, 1H), 5.85 (p, J=1.4 Hz, 1H), 5.00 (s, 2H), 4.74 (s, 2H), 3.80 (d, J=1.5 Hz, 2H), 3.50 (d, J=1.0 Hz, 3H), 2.28 (td, J=7.6, 1.4 Hz, 2H), 1.67-1.44 (m, 4H), 0.94 (dd, J=7.8, 6.8 Hz, 3H).

Synthesis of 1-[[2-(methoxymethyl)-6-methyl-imidazo[2,1-b][1,3,4]thiadiazol-5-yl]methyl]-3-(2,2,2-trifluoroethyl)-2H-pyrrol-5-one 9 a gradient from 0% to 5% methanol in DCM over 12 CV). The purest fractions were evaporated until dryness to give tert-butyl (4S)-2-oxo-4-(2,2,2-trifluoroethyl)pyrrolidine-1-carboxylate) XXV (24.5 g, 91.5 mmol) as a white solid.

Yield: 51%

$^1$H NMR (400 MHz, DMSO-d$_6$) δ 3.83 (dd, J=10.4, 7.7 Hz, 1H), 3.37 (dd, J=10.4, 8.3 Hz, 1H), 2.67-2.52 (m, 2H), 2.49-2.31 (m, 3H), 1.44 (s, 9H).

The following compounds were prepared according to the same procedure:

| No | Name | Yield |
|---|---|---|
| XXV-A | tert-butyl 4-(2-chloro-2,2-difluoro-ethyl)-2-oxo-pyrrolidine-1-carboxylate | 85% |

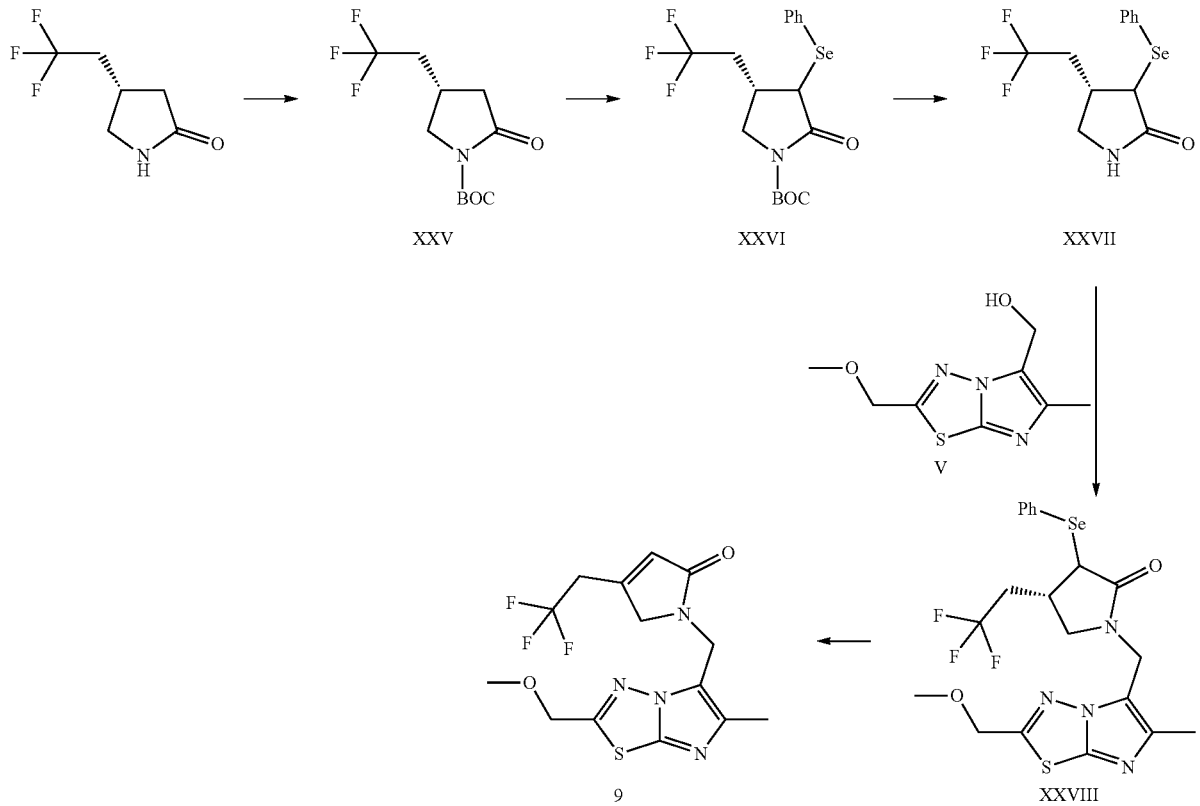

4.1. Synthesis of tert-butyl (4S)-2-oxo-4-(2,2,2-trifluoroethyl)pyrrolidine-1-carboxylate XXV To a mixture of (4S)-4-(2,2,2-trifluoroethyl)pyrrolidin-2-one (WO2011/047860, CAS1444464-14-5, 1 eq., 30 g, 179 mmol) and 4-dimethylaminopyridine (1.5 eq., 33 g, 267 mmol) in acetonitrile (900 mL), at 0° C., was added di-tert-butyl dicarbonate (1.2 eq., 48 g, 213 mmol). The mixture was then allowed to warm up to room temperature and stirred for 4 h. The solvent was evaporated under vacuum and water was added to the obtained mixture. The aqueous layer was extracted with ethyl acetate (2 times) and he combined organic layers were washed with brine, dried over MgSO$_4$, filtered and evaporated until dryness to give a yellow oil.

The crude mixture was purified by normal phase flash chromatography Biotage Isolera Four (SNAP SiO$_2$ 100 g in -continued

| No | Name | Yield |
|---|---|---|
| XXV-B | tert-butyl 2-oxo-4-(3,3,3-trifluoropropyl) pyrrolidine-1-carboxylate | 38% |
| XXV-C | tert-butyl 4-(2,2-difluoropropyl)-2-oxo-pyrrolidine-1-carboxylate | 95% |

4.2. Synthesis of tert-butyl (4S)-2-oxo-3-phenylselanyl-4-(2,2,2-trifluoroethyl)pyrrolidine-1-carboxylate XXVI To a solution of tert-butyl (4S)-2-oxo-4-(2,2,2-trifluoroethyl)pyrrolidine-1-carboxylate XXV (1 eq., 10 g, 37.4 mmol) in tetrahydrofuran (250 mL), at −78° C., was added lithium bis(trimethylsilyl)amide (2 eq., 52 mL, 75.4 mmol, 1.45 mol/L) and the mixture was stirred at −78° C. for 1 h. Then, at −78° C., was added phenylselenenyl chloride (1.1 eq., 8.0 g, 41.7 mmol) in tetrahydrofuran (85 mL) and the mixture was stirred at −78° C. for 1 h. Water was then added to the stirred solution and the aqueous layer was extracted with ethyl acetate (3 times), dried over MgSO$_4$, filtered and evaporated until dryness to give a brown oil (15 g) which was purified by normal phase flash chromatography Biotage Isolera Four (SNAP SiO$_2$ 340 g in a gradient from 10% to 20% ethyl acetate in heptane over 12CV). The purest fractions were evaporated until dryness to give tert-butyl (4S)-2-oxo-3-phenylselanyl-4-(2,2,2-trifluoroethyl)pyrrolidine-1-carboxylate XXVI (6.2 g, 14 mmol) as a clear yellow oil.

Yield: 38%

LC/MS: [M+H]$^+$=446.02

The following compounds were prepared according to the same procedure:

| No | From | Name | Yield | LC/MS [M + H]$^+$ |
|---|---|---|---|---|
| XXVI-A | XXV-A | tert-butyl 4-(2-chloro-2,2-difluoro-ethyl)-2-oxo-3-phenylselanyl-pyrrolidine-1-carboxylate | 44% | 461.9 |
| XXVI-B | XXV-B | tert-butyl 2-oxo-3-phenylselanyl-4-(3,3,3-trifluoropropyl)pyrrolidine-1-carboxylate | 53% | 460.0 |
| XXVI-C | XXV-C | tert-butyl 4-(2,2-difluoropropyl)-2-oxo-3-phenylselanyl-pyrrolidine-1-carboxylate | 70% | 442.2 |

4.3. Synthesis of (4S)-3-phenylselanyl-4-(2,2,2-trifluoroethyl)pyrrolidin-2-one XXVII To a mixture of tert-butyl (4S)-2-oxo-3-phenylselanyl-4-(2,2,2-trifluoroethyl)pyrrolidine-1-carboxylate XXVI (1 eq., 6.2 g, 15 mmol) in dichloromethane (150 mL), at 0° C., was added trifluoroacetic acid (14 eq., 15 mL, 200 mmol) and the mixture was stirred for 30 min at room temperature. The mixture was evaporated until dryness, diluted with water and neutralised with NaHCO$_3$ solid until pH=6-7. The organic layer was extracted with ethyl acetate (3 times), dried over MgSO$_4$, filtered and evaporated until dryness to give (4S)-3-phenylselanyl-4-(2,2,2-trifluoroethyl)pyrrolidin-2-one)(XVII (4.5 g, 14 mmol) as a white solid. The product was used as such in the next step without any further purification Yield: 95%

LC/MS: [M+H]$^+$=324.0

The following compounds were prepared according to the same procedure:

| No | From | Name | Yield | LC/MS [M + H]$^+$ |
|---|---|---|---|---|
| XXVII-A | XXVI-A | 4-(2-chloro-2,2-difluoro-ethyl)-3-phenylselanyl-pyrrolidin-2-one | 95% | 339.9 |
| XXVII-B | XXVI-B | 3-phenylselanyl-4-(3,3,3-trifluoropropyl)pyrrolidin-2-one | 70% | — |
| XXVII-C | XXVI-C | 4-(2,2-difluoropropyl)-3-phenylselanyl-pyrrolidin-2-one | 50% | 319.9 |

4.4. Synthesis of (4S)-1-[[2-(methoxymethyl)-6-methyl-imidazo[2,1-b][1,3,4]thiadiazol-5-yl]methyl]-3-phenylselanyl-4-(2,2,2-trifluoroethyl)pyrrolidin-2-one XXVIII A mixture of p-toluenesulfonic acid monohydrate (0.7 eq., 1.3 g, 6.8 mmol), [2-(methoxymethyl)-6-methyl-imidazo[2,1-b][1,3,4]thiadiazol-5-yl]methanol V (1 eq., 2 g, 9.37 mmol) and 3-phenylselanyl-4-(2,2,2-trifluoroethyl)pyrrolidin-2-one)(XVII (1 eq., 3 g, 9.31 mmol) in sulfolane (95 ml) was stirred at 130° C. for 16 h. The mixture was poured into water, a saturated aqueous solution of NaHCO$_3$ was added until pH=6-7. The organic layer was extracted with MTBE (2 times). The combined organic layer were washed with water (3 times), dried over MgSO$_4$, filtered and evaporated until dryness to give a brown oil. The brown oil was purified by preparative LC YMC Triart C18 (80×204-10 μm-500 g in a gradient from 60% to 90% ACN in water) to give (4S)-1-[[2-(methoxymethyl)-6-methyl-imidazo[2,1-b][1,3,4]thiadiazol-5-yl]methyl]-3-phenylselanyl-4-(2,2,2-trifluoroethyl)pyrrolidin-2-one XXVIII (450 mg, 0.82 mmol) as a brown oil.

Yield: 9%

LC/MS: [M+H]$^+$=519.02

The following compounds were prepared according to the same procedure:

| No | Int. 1 | Int. 2 | Name | Yield | LC/MS [M + H]$^+$ |
|---|---|---|---|---|---|
| XXVIII-A | XXVII | VII | 1-[[6-(difluoromethyl)-2-(methoxymethyl)imidazo[2,1-b][1,3,4]thiadiazol-5-yl]methyl]-3-phenylselanyl-4-(2,2,2-trifluoroethyl)pyrrolidin-2-one | 12% | 554.9 |
| XXVIII-B | XXVII | VII-A | 1-[[6-(1-fluorocyclopropyl)-2-(methoxymethyl)imidazo[2,1-b][1,3,4]thiadiazol-5-yl]methyl]-3-phenylselanyl-4-(2,2,2-trifluoroethyl)pyrrolidin-2-one | 19% | 563.0 |
| XXVIII-C | XXVII-A | IX | 4-(2-chloro-2,2-difluoro-ethyl)-1-[[2-(methoxymethyl)-6-(trifluoromethyl)imidazo[2,1-b][1,3,4]thiadiazol-5-yl]methyl]-3-phenylselanyl-pyrrolidin-2-one | 5% | 588.9 |
| XXVIII-D | XXVII-B | V | 1-[[2-(methoxymethyl)-6-methyl-imidazo[2,1-b][1,3,4]thiadiazol-5-yl]methyl]-3-phenylselanyl-4-(3,3,3-trifluoropropyl)pyrrolidin-2-one | 10% | 533.0 |

| No | Int. 1 | Int. 2 | Name | Yield | LC/MS [M + H]+ |
|---|---|---|---|---|---|
| XXVIII-E | XXVII-B | VII | 1-[[6-(difluoromethyl)-2-(methoxymethyl)imidazo[2,1-b][1,3,4]thiadiazol-5-yl]methyl]-3-phenylselanyl-4-(3,3,3-trifluoropropyl)pyrrolidin-2-one | 9% | 569.0 |
| XXVIII-F | XXVII-C | IX | 4-(2,2-difluoropropyl)-1-[[2-(methoxymethyl)-6-(trifluoromethyl)imidazo[2,1-b][1,3,4thiadiazol-5-yl]methyl]-3-phenylselanyl-pyrrolidin-2-one | 21% | 568.9 |
| XXVIII-G | XXVII-C | VII | 1-[[6-(difluoromethyl)-2-(methoxymethyl)imidazo[2,1-b][1,3,4-thiadiazol-5-yl]methyl]-4-(2,2-difluoropropyl)-3-phenylselanyl-pyrrolidin-2-one | 12% | 551.0 |

4.5. Synthesis of 1-[[2-(methoxymethyl)-6-methyl-imidazo[2,1-b][1,3,4]thiadiazol-5-yl]methyl]-3-(2,2,2-trifluoroethyl)-2H-pyrrol-5-one 9

To a solution of (4S)-1-[[2-(methoxymethyl)-6-methyl-imidazo[2,1-b][1,3,4]thiadiazol-5-yl]methyl]-3-phenylselanyl-4-(2,2,2-trifluoroethyl)pyrrolidin-2-one XXVIII (1 eq., 430 mg, 0.8311 mmol) in a mixture of methanol (5.5 ml) and water (1.1 mL), was added, at room temperature, sodium periodate (9 eq., 1.6 mg, 7.48 mmol). The reaction was stirred at room temperature for 30 min. A saturated aqueous solution of $NH_4Cl$ was then added to the mixture and the aqueous layer was extracted with EtOAc (3 times). The combined organic layer were dried with $MgSO_4$, filtered and evaporated until dryness to give a yellow oil which was purified by reverse phase flash chromatography Biotage Isolera Four in neutral conditions (C18 SNAP 30 g gel column in a gradient from 5% to 95% ACN in Water over 12 CV). The purest fractions were directly lyophilized to give 1-[[2-(methoxymethyl)-6-methyl-imidazo[2,1-b][1,3,4]thiadiazol-5-yl]methyl]-3-(2,2,2-trifluoroethyl)-2H-pyrrol-5-one 9 (71 mg, 0.1970 mmol) as a white solid.

Yield: 23%

LC/MS: [M+H]+=361.1

$^1$H NMR (400 MHz, DMSO-$d_6$) δ 6.08 (s, 1H), 4.77 (s, 4H), 3.99 (d, J=1.6 Hz, 2H), 3.60-3.47 (m, 2H), 3.40 (s, 3H), 2.29 (s, 3H).

The following compounds have been prepared according to the same procedure:

1-[[6-(difluoromethyl)-2-(methoxymethyl)imidazo[2,1-b][1,3,4]thiadiazol-5-yl]methyl]-3-(2,2,2-trifluoroethyl)-2H-pyrrol-5-one 10 has been prepared starting from XXVIII-A.

Yield: 45%

LC/MS: [M+H]+=397.06

$^1$H NMR (400 MHz, DMSO-$d_6$) δ 7.19 (t, J=53.4 Hz, 1H), 6.10 (s, 1H), 4.93 (s, 2H), 4.81 (s, 2H), 4.03 (d, J=1.7 Hz, 2H), 3.55 (qd, J=12.2, 11.3, 1.9 Hz, 2H), 3.42 (s, 3H).

1-[[6-(1-fluorocyclopropyl)-2-(methoxymethyl)imidazo[2,1-b][1,3,4]thiadiazol-5-yl]methyl]-3-(2,2,2-trifluoroethyl)-2H-pyrrol-5-one 11 has been prepared starting from XXVIII-B.

Yield: 9%

LC/MS: [M+H]+=405.05

$^1$H NMR (400 MHz, DMSO-$d_6$) δ 6.08 (s, 1H), 4.94 (d, J=1.5 Hz, 2H), 4.78 (s, 2H), 3.99 (d, J=1.6 Hz, 2H), 3.62-3.47 (m, 2H), 3.40 (s, 3H), 1.47-1.33 (m, 2H), 1.18 (td, J=8.4, 6.0 Hz, 2H).

3-(2-chloro-2,2-difluoro-ethyl)-1-[[2-(methoxymethyl)-6-(trifluoromethyl)imidazo[2,1-b][1,3,4]thiadiazol-5-yl]methyl]-2H-pyrrol-5-one 12 has been prepared starting from XXVIII-C.

Yield: 9%

LC/MS: [M+H]+=431.0

$^1$H NMR (400 MHz, DMSO-$d_6$) δ 6.12 (s, 1H), 4.95 (s, 2H), 4.81 (s, 2H), 4.05-3.98 (m, 2H), 3.71 (td, J=13.9, 1.2 Hz, 2H), 3.42 (s, 3H).

1-[[2-(methoxymethyl)-6-methyl-imidazo[2,1-b][1,3,4]thiadiazol-5-yl]methyl]-3-(3,3,3-trifluoropropyl)-2H-pyrrol-5-one 13 has been prepared starting from XXVIII-D.

Yield: 53%

LC/MS: [M+H]+=375.0

$^1$H NMR (400 MHz, DMSO-$d_6$) δ 5.91 (t, J=1.5 Hz, 1H), 4.77 (s, 2H), 4.72 (s, 2H), 3.92 (d, J=1.5 Hz, 2H), 3.40 (s, 3H), 2.53 (d, J=5.6 Hz, 4H), 2.27 (s, 3H).

1-[[6-(difluoromethyl)-2-(methoxymethyl)imidazo[2,1-b][1,3,4]thiadiazol-5-yl]methyl]-3-(3,3,3-trifluoropropyl)-2H-pyrrol-5-one 14 has been prepared starting from XXVIII-E.

Yield: 52%

LC/MS: [M+H]+=411.07

$^1$H NMR (500 MHz, DMSO-$d_6$) δ 7.17 (t, J=53.4 Hz, 1H), 5.94 (s, 1H), 4.89 (s, 2H), 4.82 (s, 2H), 3.96 (s, 2H), 3.45 (s, 3H), 2.54 (d, J=5.4 Hz, 4H).

3-(2,2-difluoropropyl)-1-[[2-(methoxymethyl)-6-(trifluoromethyl)imidazo[2,1-b][1,3,4]thiadiazol-5-yl]methyl]-2H-pyrrol-5-one 15 has been prepared starting from XXVIII-F.

Yield: 41%

LC/MS: [M+H]+=410.9

$^1$H NMR (400 MHz, DMSO-$d_6$) δ 6.00 (s, 1H), 4.94 (s, 2H), 4.82 (s, 2H), 3.97 (d, J=1.6 Hz, 2H), 3.43 (s, 3H), 3.06 (t, J=16.8 Hz, 2H), 1.62 (t, J=18.9 Hz, 3H).

1-[[6-(difluoromethyl)-2-(methoxymethyl)imidazo[2,1-b][1,3,4]thiadiazol-5-yl]methyl]-3-(2,2-difluoropropyl)-2H-pyrrol-5-one has been prepared 16 starting from XXVIII-G.

Yield: 14%

LC/MS: [M+H]+=396.0

¹H NMR (400 MHz, DMSO-d₆) δ 7.17 (t, J=53.4 Hz, 1H), 6.00 (s, 1H), 4.94 (s, 2H), 4.82 (s, 2H), 3.97 (d, J=1.6 Hz, 2H), 3.43 (s, 3H), 3.06 (t, J=16.8 Hz, 2H), 1.62 (t, J=18.9 Hz, 3H).

Synthesis of 3-[(1R)-2,2-difluorocyclopropyl]-1-[[2-(methoxymethyl)-6-(trifluoromethyl)imidazo[2,1-b][1,3,4]thiadiazol-5-yl]methyl]-2H-pyrrol-5-one 17A and 3-[(1S)-2,2-difluorocyclopropyl]-1-[[2-(methoxymethyl)-6-(trifluoromethyl)imidazo[2,1-b][1,3,4]thiadiazol-5-yl]methyl]-2H-pyrrol-5-one 17B with brine, dried over MgSO₄, filtered and evaporated until dryness (25° C. maximum) to give a brown oil. The brown oil was purified by reverse phase flash chromatography Biotage Isolera Four in neutral mode (SNAP C18 60 g column with a gradient from 5% to 95% of ACN over 10 CV) and the purest fractions were lyophilized to give 3-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one 17 (570 mg, 1.35 mmol) as a white solid.

Yield: 55%

LC/MS: [M+H]⁺=409.1

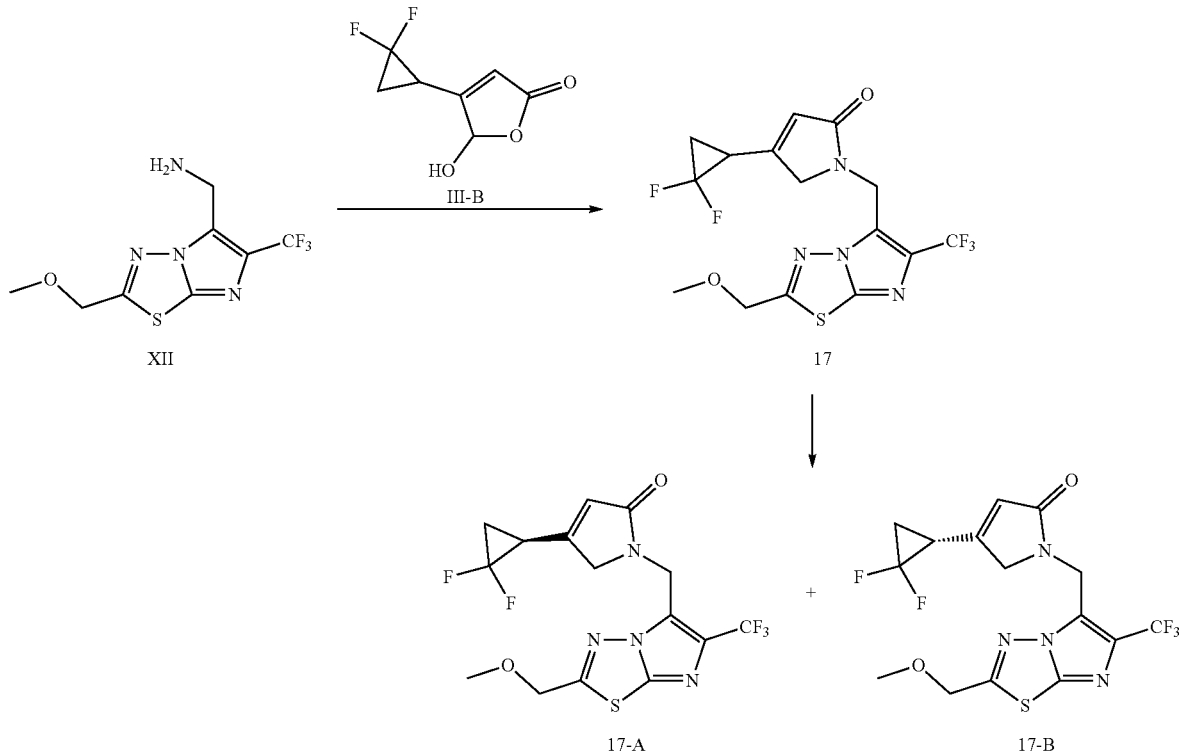

5.1. Synthesis of 3-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one 17

To a solution of [2-(methoxymethyl)-6-(trifluoromethyl)imidazo[2,1-b][1,3,4]thiadiazol-5-yl]methanamine XII (1 eq., 700 mg, 2.44 mmol, 93 mass %) in 2-propanol (12 mL), at room temperature, was added 3-(2,2-difluorocyclopropyl)-2-hydroxy-2H-furan-5-one III-B (1 eq., 500 mg, 2.44 mmol, 80 mass %) and the reaction was stirred at room temperature during 1 h. A solution of sodium borohydride (1 eq., 92 mg, 2.44 mmol) in water (3.5 mL) was then added to the mixture at room temperature and the reaction was stirred at room temperature during 2 h. An additional quantity of sodium borohydride (1 eq., 92 mg, 2.44 mmol) was then added to the mixture and the reaction was stirred at room temperature during 15 min. A third quantity of sodium borohydride (1 eq., 92 mg, 2.44 mmol) was added followed by acetic acid (35 eq., 5 mL, 87.08 mmol) and the mixture was stirred at room temperature during 1 h. A saturated aqueous solution of NaHCO₃ was added to the mixture cooled to 0° C. and the aqueous layer was extracted with MTBE (2 times). The combined organic layers were washed ¹H NMR (400 MHz, DMSO-d₆) δ 6.02 (s, 1H), 5.03-4.86 (m, 2H), 4.83 (s, 2H), 3.97 (d, J=1.5 Hz, 2H), 3.43 (s, 3H), 2.77 (td, J=12.0, 8.0 Hz, 1H), 2.09-1.82 (m, 2H).

The mixture of enantiomers (105 mg) was separated by chiral SFC (AS 50×265-5 μm-300g*EtOH 10%, 360 mL/min., 35° C.) to give 3-[2,2-difluorocyclopropyl]-1-[[2-(methoxymethyl)-6-(trifluoromethyl)imidazo[2,1-b][1,3,4]thiadiazol-5-yl]methyl]-2H-pyrrol-5-one (enantiomer 17-A, first eluted, 27 mg, 0.066 mmol) and 3-[2,2-difluorocyclopropyl]-1-[[2-(methoxymethyl)-6-(trifluoromethyl)imidazo[2,1-b][1,3,4]thiadiazol-5-yl]methyl]-2H-pyrrol-5-one (enantiomer 17-B, second eluted, 27 mg, 0.066 mmol).

Analytical Chiral SFC (Column AS, 3 mL/min., 30° C., 20% MeOH, 100 bar): enantiomer 17-A: 1.19 min, enantiomer 17-B: 1.63 min After separation, both enantiomers were repurified by reverse phase flash chromatography Biotage Isolera Four in neutral mode (SNAP C18 12 g column with a gradient from 5% to 95% of ACN in water over 10 CV) and directly lyophilized.

The following compounds have been prepared according to the same procedure:

3-(2,2-difluorocyclopropyl)-1-[[2-(methoxymethyl)-6-methyl-imidazo[2,1-b][1,3,4]thiadiazol-5-yl]methyl]-2H-pyrrol-5-one 18 has been prepared starting from XIII and III-B.

Yield: 50%

LC/MS: [M+H]+=355.04

1H NMR (400 MHz, DMSO-d6) δ 6.00 (s, 1H), 4.76 (d, J=13.0 Hz, 4H), 3.96 (d, J=1.5 Hz, 2H), 3.40 (s, 3H), 2.76 (td, J=12.1, 8.1 Hz, 1H), 2.28 (s, 3H), 2.08-1.81 (m, 2H).

The mixture of enantiomers (110 mg) was separated by chiral SFC (AS 50×265-5 μm-300 g*MeOH 10%, 360 mL/min., 35° C.) to give 1-[[2-(methoxymethyl)-6-methyl-imidazo[2,1-b][1,3,4]thiadiazol-5-yl]methyl]-3-[2,2-difluorocyclopropyl]-2H-pyrrol-5-one (enantiomer 18-A, first eluted, 15 mg, 0.042 mmol) and 1-[[2-(methoxymethyl)-6-methyl-imidazo[2,1-b][1,3,4]thiadiazol-5-yl]methyl]-3-[2,2-difluorocyclopropyl]-2H-pyrrol-5-one (enantiomer 18-B, second eluted, 19 mg, 0.053 mmol).

Analytical Chiral SFC (Column AS, 3 mL/min., 30° C., 20% MeOH, 100 bar): enantiomer 18-A: 1.04 min, enantiomer 18-B: 1.31 min After separation, both enantiomers were purified by reverse phase flash chromatography Biotage Isolera Four in neutral mode (SNAP C18 12 g column with a gradient from 5% to 95% of ACN in water over 10 CV) and directly lyophilized.

3-(2,2-difluorocyclopropyl)-1-[[6-(difluoromethyl)-2-(methoxymethyl)imidazo[2,1-b][1,3,4]thiadiazol-5-yl]methyl]-2H-pyrrol-5-one 19 has been prepared starting from XXIII (as a free base) and III-B.

Yield: 11%

LC/MS: [M+H]+=391.06

1H NMR (400 MHz, CDCl3) δ 6.87 (t, J=54.6 Hz, 1H), 5.99 (s, 1H), 5.01 (s, 2H), 4.74 (s, 2H), 4.01-3.78 (m, 2H), 3.51 (s, 3H), 2.42 (td, J=11.7, 7.8 Hz, 1H), 1.87 (tdd, J=11.7, 8.0, 5.3 Hz, 1H), 1.51 (dp, J=12.5, 4.4, 4.0 Hz, 1H).

The mixture of enantiomers (138 mg) was separated by chiral SFC (AS 50×265-5 μm-300 g*EtOH 15%, 360 mL/min., 35° C.) to give 1-[[6-(difluoromethyl)-2-(methoxymethyl)imidazo[2,1-b][1,3,4]thiadiazol-5-yl]methyl]-3-[2,2-difluorocyclopropyl]-2H-pyrrol-5-one (enantiomer 19-A, first eluted, 15 mg, 0.038 mmol) and 3-[2,2-difluorocyclopropyl]-1-[[6-(difluoromethyl)-2-(methoxymethyl)imidazo[2,1-b][1,3,4]thiadiazol-5-yl]methyl]-2H-pyrrol-5-one (enantiomer 19-B, second eluted, 19 mg, 0.048 mmol).

Analytical Chiral SFC (Column AS, 3 mL/min., 30° C., 20% EtOH, 100 bar): enantiomer 19-A: 1.39 min, enantiomer 19-B: 1.87 min After separation, both enantiomers were purified by reverse phase flash chromatography Biotage Isolera Four in neutral mode (SNAP C18 12 g column with a gradient from 5% to 95% of ACN in water over 10 CV) and directly lyophilized.

3-(2,2-difluoropropyl)-1-[[2-(methoxymethyl)-6-methyl-imidazo[2,1-b][1,3,4]thiadiazol-5-yl]methyl]-2H-pyrrol-5-one 20 has been prepared according to the same method starting from XIII and II-A Yield: 16%

LC/MS: [M+H]+=357.12

1H NMR (400 MHz, DMSO-d6) δ 5.99 (t, J=1.5 Hz, 1H), 4.76 (d, J=5.6 Hz, 3H), 3.99-3.93 (m, 2H), 3.40 (s, 3H), 3.06 (t, J=16.9 Hz, 2H), 2.28 (s, 3H), 1.62 (t, J=18.9 Hz, 3H).

Synthesis of 1-[[2-(hydroxymethyl)-6-methyl-imidazo[2,1-b][1,3,4]thiadiazol-5-yl]methyl]-3-(3,3,3-trifluoropropyl)-2H-pyrrol-5-one 21

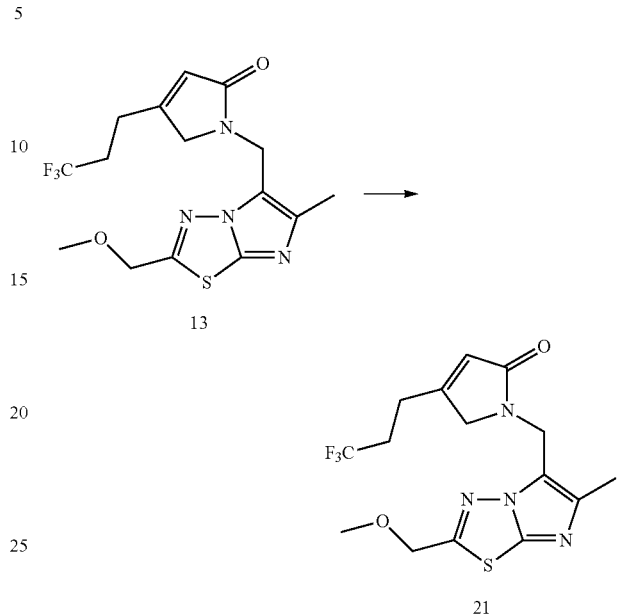

To a mixture of 1-[[2-(methoxymethyl)-6-methyl-imidazo[2,1-b][1,3,4]thiadiazol-5-yl]methyl]-3-(3,3,3-trifluoropropyl)-2H-pyrrol-5-one 13 (1 eq., 100 mg, 0.26 mmol) in dichloromethane (1.5 mL) was added at room temperature boron tribromide (5 eq., 1.3 mL, 1.3 mmol) then the mixture was stirred for 1 h. Methanol was slowly added to mixture (exothermic reaction), then the solvents were evaporated until dryness to give a yellow oil. The yellow oil was purified by reverse phase flash chromatography Biotage Isolera Four in neutral conditions (SNAP 30 g C18 from in a gradient from 10% to 95% of ACN in water). The purest fractions were combined and lyophilized to give 1-[[2-(hydroxymethyl)-6-methyl-imidazo[2,1-b][1,3,4]thiadiazol-5-yl]methyl]-3-(3,3,3-trifluoropropyl)-2H-pyrrol-5-one 21 (26 mg, 0.07 mmol) as a white solid Yield: 27%

LC/MS: [M+H]+=361.08

1H NMR (400 MHz, DMSO-d6) δ 6.34 (s, 1H), 5.92 (t, J=1.4 Hz, 1H), 4.78 (s, 2H), 4.71 (s, 2H), 3.91 (d, J=1.6 Hz, 2H), 2.59-2.52 (m, 4H), 2.27 (s, 3H).

1-[[6-(difluoromethyl)-2-(hydroxymethyl)imidazo[2,1-b][1,3,4]thiadiazol-5-yl]methyl]-3-(3,3,3-trifluoropropyl)-2H-pyrrol-5-one 22 has been prepared according to the same method starting from 14.

Yield: 6%

LC/MS: [M+H]+=396.99

1H NMR (400 MHz, DMSO-d6) δ 7.16 (t, J=53.4 Hz, 1H), 6.47 (s, 1H), 5.94 (t, J=1.5 Hz, 1H), 4.87 (s, 2H), 4.82 (d, J=4.5 Hz, 2H), 3.95 (d, J=1.6 Hz, 2H), 2.54 (d, J=5.7 Hz, 4H).

1-[[6-(difluoromethyl)-2-(hydroxymethyl)imidazo[2,1-b][1,3,4]thiadiazol-5-yl]methyl]-3-(2,2,2-trifluoroethyl)-2H-pyrrol-5-one 23 has been prepared according to the same method starting from 10.

Yield: 14%

LC/MS: [M+H]+=383.03

1H NMR (400 MHz, DMSO-d6) δ 7.17 (t, J=53.4 Hz, 1H), 6.48 (s, 1H), 6.09 (s, 1H), 4.91 (s, 2H), 4.82 (s, 2H), 4.08-3.92 (m, 2H), 3.60-3.47 (m, 2H).

Table (I) indicates the IUPAC name (or the name generated from Accelerys Draw 4.0 or Biovia Draw 16.1) of the compound, the ion peak observed in mass spectroscopy and the 1H NMR description.

TABLE I

| | | Examples | | |
|---|---|---|---|---|
| no | Compound NAME | Structure | MS (MH$^+$) | $^1$H NMR |
| 1 | 1-[[2-(methoxymethyl)-6-(trifluoromethyl)imidazo[2,1-b][1,3,4]thiadiazol-5-yl]methyl]-3-propyl-2H-pyrrol-5-one | | 375 | 5.71 (s, 1 H), 4.82 (s, 2 H), 4.75 (s, 2 H), 3.80 (s, 2 H), 3.35 (s, 3 H), 2.19 (t, J = 7.5 Hz, 2 H), 1.40 (m, 2 H), 0.79 (t, J = 7.3 Hz, 3 H) |
| 2 | 1-[[2-(methoxymethyl)-6-(trifluoromethyl)imidazo[2,1-b][1,3,4]thiadiazol-5-yl]methyl]-3-(2,2,2-trifluoroethyl)-2H-pyrrol-5-one | | 415 | 6.09 (s, 1 H), 4.95 (s, 2 H), 4.82 (s, 2 H), 4.00 (s, 2 H), 3.55 (q, 2 H), 3.43 (s, 3 H) |
| 3 | 1-[[2-(methoxymethyl)-6-(trifluoromethyl)imidazo[2,1-b][1,3,4]thiadiazol-5-yl]methyl]-3-(3,3,3-trifluoropropyl)-2H-pyrrol-5-one | | 429 | 5.95 (s, 1H), 4.92 (s, 2H), 4.82 (s, 2H), 3.94 (s, 2H), 3.45 (s, 3H), 2.45 (m, 4H) |
| 4 | 1-[[2-(methoxymethyl)-6-methyl-imidazo[2,1-b][1,3,4]thiadiazol-5-yl]methyl]-3-propyl-2H-pyrrol-5-one | | 321 | 5.78 (s, 1H), 4.77 (s, 2H), 4.72 (s, 2H), 3.87 (s, 2H), 3.40 (s, 3H), 2.27 (d, J = 4.1 Hz, 5H), 1.48 (h, J = 7.4 Hz, 2H), 0.87 (t, J = 7.3 Hz, 3H) |
| 5 | 1-[[6-chloro-2-(methoxymethyl)imidazo[2,1-b][1,3,4]thiadiazol-5-yl]methyl]-3-(2,2,2-trifluoroethyl)-2H-pyrrol-5-one | | 381/383 | 6.08 (s, 1H), 4.80 (s, 4H), 4.02 (s, 2H), 3.55 (q, 2H), 3.40 (s, 3H) |
| 6 | 1-[[6-chloro-2-(methoxymethyl)imidazo[2,1-b][1,3,4]thiadiazol-5-yl]methyl]-3-propyl-2H-pyrrol-5-one | | 341/343 | 5.78 (s, 1H), 4.83 (s, 2H), 4.77 (s, 2H), 3.91 (s, 2H), 3.43 (s, 3H), 2.28 (dd, 2H), 1.48 (m, 2H), 0.87 (t, 3H) |

TABLE I-continued

Examples

| no | Compound NAME | Structure | MS (MH+) | ¹H NMR |
|---|---|---|---|---|
| 7 | 1-[[6-chloro-2-(methoxymethyl)imidazo[2,1-b][1,3,4]thiadiazol-5-yl]methyl]-3-(3,3,3-trifluoropropyl)-2H-pyrrol-5-one | 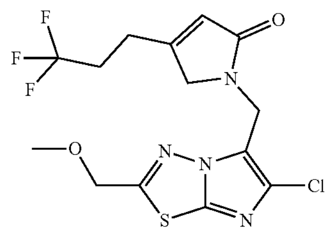 [SMILES: COCc1nn2c(CN3CC(CCC(F)(F)F)=CC3=O)c(Cl)nc2s1] | 395/397 | 5.94 (s, 1H), 4.80 (s, 2H), 4.75 (s, 2H), 3.96 (s, 2H), 3.43 (q, 2H), 3.56 (s, 3H) |
| 8 | 1-[[6-(difluoromethyl)-2-(methoxymethyl)imidazo[2,1-b][1,3,4]thiadiazol-5-yl]methyl]-3-propyl-2H-pyrrol-5-one | 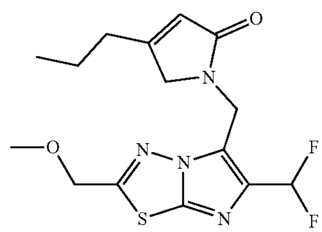 [SMILES: CCCC1=CC(=O)N(Cc2c(C(F)F)nc3sc(COC)nn23)C1] | 357 | 6.88 (t, J = 54.5 Hz, 1H), 5.85 (p, J = 1.4 Hz, 1H), 5.00 (s, 2H), 4.74 (s, 2H), 3.80 (d, J = 1.5 Hz, 2H), 3.50 (d, J = 1.0 Hz, 3H), 2.28 (td, J = 7.6, 1.4 Hz, 2H), 1.67-1.44 (m, 4H), 0.94 (dd, J = 7.8, 6.8 Hz, 3H) |
| 9 | 1-[[2-(methoxymethyl)-6-methyl-imidazo[2,1-b][1,3,4]thiadiazol-5-yl]methyl]-3-(2,2,2-trifluoroethyl)-2H-pyrrol-5-one | 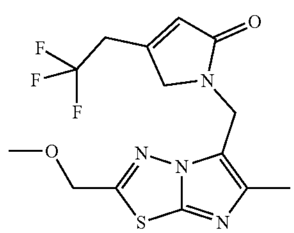 | 361 | 6.08 (s, 1H), 4.77 (s, 4H), 3.99 (d, J = 1.6 Hz, 2H), 3.60-3.47 (m, 2H), 3.40 (s, 3H), 2.29 (s, 3H). |
| 10 | 1-[[6-(difluoromethyl)-2-(methoxymethyl)imidazo[2,1-b][1,3,4]thiadiazol-5-yl]methyl]-3-(2,2,2-trifluoroethyl)-2H-pyrrol-5-one | 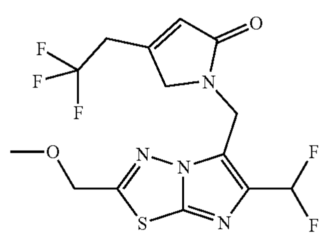 [SMILES: COCc1nn2c(CN3CC(CC(F)(F)F)=CC3=O)c(C(F)F)nc2s1] | 397 | 7.19 (t, J = 53.4 Hz, 1H), 6.10 (s, 1H), 4.93 (s, 2H), 4.81 (s, 2H), 4.03 (d, J = 1.7 Hz, 2H), 3.55 (qd, J = 12.2, 11.3, 1.9 Hz, 2H), 3.42 (s, 3H) |
| 11 | 1-[[6-(1-fluorocyclopropyl)-2-(methoxymethyl)imidazo[2,1-b][1,3,4]thiadiazol-5-yl]methyl]-3-(2,2,2-trifluoroethyl)-2H-pyrrol-5-one | 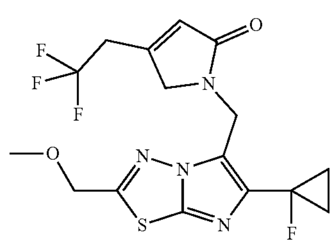 [SMILES: COCc1nn2c(CN3CC(CC(F)(F)F)=CC3=O)c(C3(F)CC3)nc2s1] | 405 | 6.08 (s, 1H), 4.94 (d, J = 1.5 Hz, 2H), 4.78 (s, 2H), 3.99 (d, J = 1.6 Hz, 2H), 3.62-3.47 (m, 2H), 3.40 (s, 3H), 1.47-1.33 (m, 2H), 1.18 (td, J = 8.4, 6.0 Hz, 2H) |
| 12 | 3-(2-chloro-2,2-difluoro-ethyl)-1-[[2-(methoxymethyl)-6-(trifluoromethyl)imidazo[2,1-b][1,3,4]thiadiazol-5-yl]methyl]-2H-pyrrol-5-one | 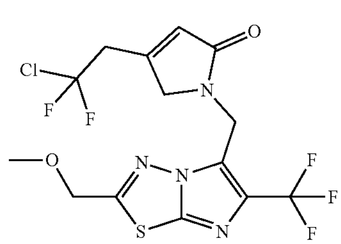 [SMILES: COCc1nn2c(CN3CC(CC(F)(F)Cl)=CC3=O)c(C(F)(F)F)nc2s1] | 431 | 6.12 (s, 1H), 4.95 (s, 2H), 4.81 (s, 2H), 4.05-3.98 (m, 2H), 3.71 (td, J = 13.9, 1.2 Hz, 2H), 3.42 (s, 3H) |

TABLE I-continued

Examples

| no | Compound NAME | Structure | MS (MH+) | 1H NMR |
|---|---|---|---|---|
| 13 | 1-[[2-(methoxymethyl)-6-methyl-imidazo[2,1-b][1,3,4]thiadiazol-5-yl]methyl]-3-(3,3,3-trifluoropropyl)-2H-pyrrol-5-one | 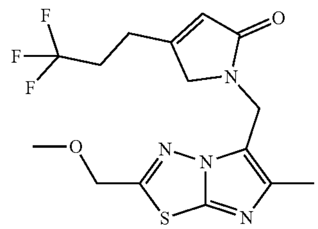 [SMILES: COCc1nn2c(CN3CC(CCC(F)(F)F)=CC3=O)c(C)nc2s1] | 375 | 5.91 (t, J = 1.5 Hz, 1H), 4.77 (s, 2H), 4.72 (s, 2H), 3.92 (d, J = 1.5 Hz, 2H), 3.40 (s, 3H), 2.53 (d, J = 5.6 Hz, 4H), 2.27 (s, 3H) |
| 14 | 1-[[6-(difluoromethyl)-2-(methoxymethyl)imidazo[2,1-b][1,3,4]thiadiazol-5-yl]methyl]-3-(3,3,3-trifluoropropyl)-2H-pyrrol-5-one | 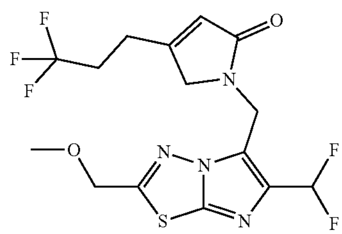 [SMILES: COCc1nn2c(CN3CC(CCC(F)(F)F)=CC3=O)c(C(F)F)nc2s1] | 411 | 7.17 (t, J = 53.4 Hz, 1H), 5.94 (s, 1H), 4.89 (s, 2H), 4.82 (s, 2H), 3.96 (s, 2H), 3.45 (s, 3H), 2.54 (d, J = 5.4 Hz, 4H) |
| 15 | 3-(2,2-difluoropropyl)-1-[[2-(methoxymethyl)-6-(trifluoromethyl)imidazo[2,1-b][1,3,4]thiadiazol-5-yl]methyl]-2H-pyrrol-5-one | 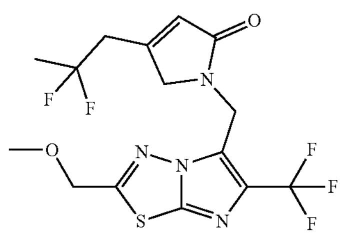 [SMILES: COCc1nn2c(CN3CC(CC(C)(F)F)=CC3=O)c(C(F)(F)F)nc2s1] | 411 | 6.00 (s, 1H), 4.94 (s, 2H), 4.82 (s, 2H), 3.97 (d, J = 1.6 Hz, 2H), 3.43 (s, 3H), 3.06 (t, J = 16.8 Hz, 2H), 1.62 (t, J = 18.9 Hz, 3H) |
| 16 | 1-[[6-(difluoromethyl)-2-(methoxymethyl)imidazo[2,1-b][1,3,4]thiadiazol-5-yl]methyl]-3-(2,2-difluoropropyl)-2H-pyrrol-5-one | 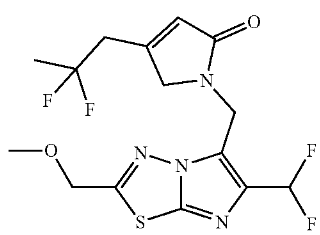 [SMILES: COCc1nn2c(CN3CC(CC(C)(F)F)=CC3=O)c(C(F)F)nc2s1] | 396 | 7.17 (t, J = 53.4 Hz, 1H), 6.00 (s, 1H), 4.94 (s, 2H), 4.82 (s, 2H), 3.97 (d, J = 1.6 Hz, 2H), 3.43 (s, 3H), 3.06 (t, J = 16.8 Hz, 2H), 1.62 (t, J = 18.9 Hz, 3H) |
| 17-A | 3-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one (enantiomer A) | 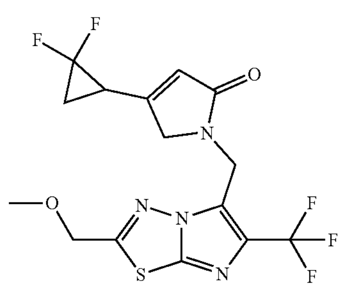 [SMILES: COCc1nn2c(CN3CC(C4CC4(F)F)=CC3=O)c(C(F)(F)F)nc2s1] | 409 | 6.02 (s, 1H), 5.03-4.86 (m, 2H), 4.83 (s, 2H), 3.97 (d, J = 1.5 Hz, 2H), 3.43 (s, 3H), 2.77 (td, J = 12.0, 8.0 Hz, 1H), 2.09-1.82 (m, 2H) |
| 17-B | 3-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one (enantiomer B) | 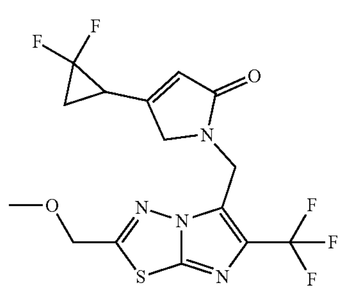 [SMILES: COCc1nn2c(CN3CC(C4CC4(F)F)=CC3=O)c(C(F)(F)F)nc2s1] | 409 | 6.02 (s, 1H), 5.03-4.86 (m, 2H), 4.83 (s, 2H), 3.97 (d, J = 1.5 Hz, 2H), 3.43 (s, 3H), 2.77 (td, J = 12.0, 8.0 Hz, 1H), 2.09-1.82 (m, 2H) |

TABLE I-continued

| no | Compound NAME | Structure | MS (MH+) | ¹H NMR |
|---|---|---|---|---|
| 18-A | 1-[[2-(methoxymethyl)-6-methyl-imidazo[2,1-b][1,3,4]thiadiazol-5-yl]methyl]-3-[2,2-difluorocyclopropyl]-2H-pyrrol-5-one (enantiomer A) | 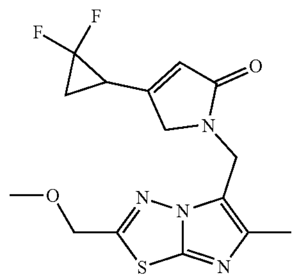 | 355 | 6.00 (s, 1H), 4.76 (d, J = 13.0 Hz, 4H), 3.96 (d, J = 1.5 Hz, 2H), 3.40 (s, 3H), 2.76 (td, J = 12.1, 8.1 Hz, 1H), 2.28 (s, 3H), 2.08-1.81 (m, 2H) |
| 18-B | 1-[[2-(methoxymethyl)-6-methyl-imidazo[2,1-b][1,3,4]thiadiazol-5-yl]methyl]-3-[2,2-difluorocyclopropyl]-2H-pyrrol-5-one (enantiomer B) | 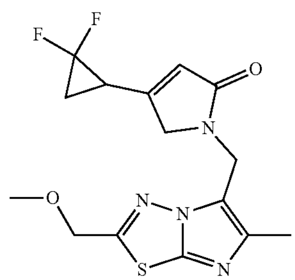 | 355 | 6.00 (s, 1H), 4.76 (d, J = 13.0 Hz, 4H), 3.96 (d, J = 1.5 Hz, 2H), 3.40 (s, 3H), 2.76 (td, J = 12.1, 8.1 Hz, 1H), 2.28 (s, 3H), 2.08-1.81 (m, 2H) |
| 19-A | 1-[[6-(difluoromethyl)-2-(methoxymethyl)imidazo[2,1-b][1,3,4]thiadiazol-5-yl]methyl]-3-[2,2-difluorocyclopropyl]-2H-pyrrol-5-one (enantiomer A) | 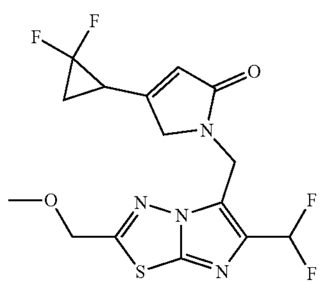 [SMILES: COCc1nn2c(CN3CC(C4CC4(F)F)=CC3=O)c(C(F)F)nc2s1] | 391 | 6.87 (t, J = 54.6 Hz, 1H), 5.99 (s, 1H), 5.01 (s, 2H), 4.74 (s, 2H), 4.01-3.78 (m, 2H), 3.51 (s, 3H), 2.42 (td, J = 11.7, 7.8 Hz, 1H), 1.87 (tdd, J = 11.7, 8.0, 5.3 Hz, 1H), 1.51 (dp, J = 12.5, 4.4, 4.0 Hz, 1H) |
| 19-B | 1-[[6-(difluoromethyl)-2-(methoxymethyl)imidazo[2,1-b][1,3,4]thiadiazol-5-yl]methyl]-3-[2,2-difluorocyclopropyl]-2H-pyrrol-5-one (enantiomer B) | 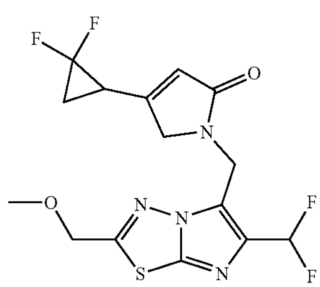 [SMILES: COCc1nn2c(CN3CC(C4CC4(F)F)=CC3=O)c(C(F)F)nc2s1] | 391 | 6.87 (t, J = 54.6 Hz, 1H), 5.99 (s, 1H), 5.01 (s, 2H), 4.74 (s, 2H), 4.01-3.78 (m, 2H), 3.51 (s, 3H), 2.42 (td, J = 11.7, 7.8 Hz, 1H), 1.87 (tdd, J = 11.7, 8.0, 5.3 Hz, 1H), 1.51 (dp, J = 12.5, 4.4, 4.0 Hz, 1H) |
| 20 | 3-(2,2-difluoropropyl)-1-[[2-(methoxymethyl)-6-methyl-imidazo[2,1-b][1,3,4]thiadiazol-5-yl]methyl]-2H-pyrrol-5-one | 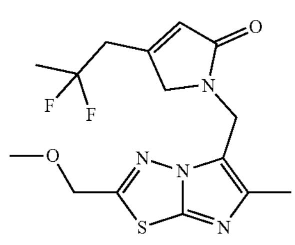 | 357 | 5.99 (t, J = 1.5 Hz, 1H), 4.76 (d, J = 5.6 Hz, 3H), 3.99-3.93 (m, 2H), 3.40 (s, 3H), 3.06 (t, J = 16.9 Hz, 2H), 2.28 (s, 3H), 1.62 (t, J = 18.9 Hz, 3H) |

TABLE I-continued

Examples

| no | Compound NAME | Structure | MS (MH+) | ¹H NMR |
|---|---|---|---|---|
| 21 | 1-[[2-(hydroxymethyl)-6-methyl-imidazo[2,1-b][1,3,4]thiadiazol-5-yl]methyl]-3-(3,3,3-trifluoropropyl)-2H-pyrrol-5-one | 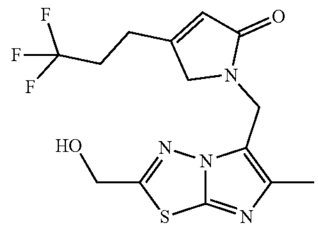 [SMILES: Cc1nc2sc(CO)nn2c1CN1CC(CCC(F)(F)F)=CC1=O] | 361 | 6.34 (s, 1H), 5.92 (t, J = 1.4 Hz, 1H), 4.78 (s, 2H), 4.71 (s, 2H), 3.91 (d, J = 1.6 Hz, 2H), 2.59-2.52 (m, 4H), 2.27 (s, 3H) |
| 22 | 1-[[6-(difluoromethyl)-2-(hydroxymethyl)imidazo[2,1-b][1,3,4]thiadiazol-5-yl]methyl]-3-(3,3,3-trifluoropropyl)-2H-pyrrol-5-one | 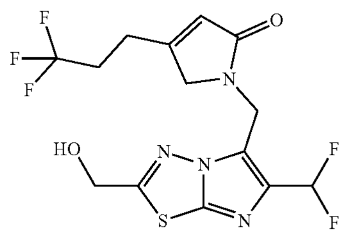 [SMILES: O=C1C=C(CCC(F)(F)F)CN1Cc1c(C(F)F)nc2sc(CO)nn12] | 397 | 7.16 (t, J = 53.4 Hz, 1H), 6.47 (s, 1H), 5.94 (t, J = 1.5 Hz, 1H), 4.87 (s, 2H), 4.82 (d, J = 4.5 Hz, 2H), 3.95 (d, J = 1.6 Hz, 2H), 2.54 (d, J = 5.7 Hz, 4H) |
| 23 | 1-[[6-(difluoromethyl)-2-(hydroxymethyl)imidazo[2,1-b][1,3,4]thiadiazol-5-yl]methyl]-3-(2,2,2-trifluoroethyl)-2H-pyrrol-5-one | 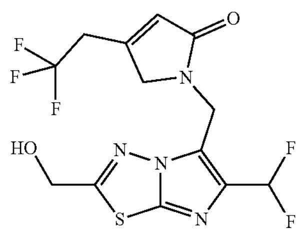 [SMILES: O=C1C=C(CC(F)(F)F)CN1Cc1c(C(F)F)nc2sc(CO)nn12] | 383 | 7.17 (t, J = 53.4 Hz, 1H), 6.48 (s, 1H), 6.09 (s, 1H), 4.91 (s, 2H), 4.82 (s, 2H), 4.08-3.92 (m, 2H), 3.60-3.47 (m, 2H) |

In Vitro and in Vivo ASSAYS

1. Binding Assays to SV2A and SV2C

Human SV2A and SV2C proteins were expressed in human embryonic kidney (HEK) cells. HEK SV2A and HEK SV2C membrane preparations were prepared as described in Gillard et al (Eur. J. Pharmacol. 2006, 536, 102-108). To measure affinity of non-labelled compounds, competition experiments were performed as follow: Membranes expressing SV2 proteins (5 to 15 µg proteins per assay) were incubated for 60 min at 37° C. with either [³H]-2-[4-(3-azidophenyl)-2-oxo-1-pyrrolidinyl]butanamide (5 nM) and/or [³H]-4R-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one (25 nM) in 0.2 ml of a 50 mM Tris-HCl buffer (pH 7.4) containing 2 mM MgCl₂, 0.1% dimethylsulfoxide and ten increasing concentrations of non-labelled test compound (0.1 nM to 10 µM). At the end of the incubation period, the membrane-bound radioligand was recovered by rapid filtration through GF/C glass fiber filters pre-soaked in 0.1% polyethyleneimine. Membranes were washed with at least 4 times the assay volume of ice-cold 50 mM Tris HCl buffer (pH 7.4). The filters were dried and the radioactivity determined by liquid scintillation. The entire filtration step did not exceed 10 sec. Measured affinity pIC₅₀ values were corrected to pKi according to Cheng and Prusoff (Biochem. Pharmacol. 1973, 22(23), 3099-3108).

Compounds of formula (I) according to the invention typically show pKi SV2A values of at least 6.5, and pKi SV2C values of at least 6.0.

Examples 18-B, 21, 22 and 23 display pki SV2A values greater than 6.5 and lower than or equal to 7.5. Examples 2, 5, 11, 18-A and 20 display pki SV2A values greater than 7.5 and lower than or equal to 8.0. Examples 1, 3, 4, 6, 7, 8, 9, 10, 11, 12, 13, 14, 15, 16, 17-A, 17-B, 19-A and 19-B display pki SV2A values greater than or equal to 8.0 and lower than 8.5

2. Seizure Models

Male NMRI mice (Charles River, Germany) weighing 22-32 g are used in all experiments. The animals are kept on a 12/12-h light/dark cycle with lights on at 6:00 am and are housed at a temperature maintained at 20-21° C. and at humidity of about 40%. The mice are housed in groups of 10 per cage (Type III). All animals have free access to standard pellet food and water before random assignment to experimental groups consisting of 10 mice each. All animal experiments are done according to the National Rules on Animal Experiments and conducted in accordance with the guidelines of the European Community Council directive 2010/63/EU. A local ethical committee approved the experimental protocols.

6.1 6 Hz Seizure Model

The 6 Hz model is carried out according to a previously described protocol (Kaminski et al., Epilepsia (2004), 45, 864-867). Briefly, corneal stimulation (44 mA, 0.2 ms-duration monopolar rectangular pulses at 6 Hz for 3 s) is delivered by a constant-current device (ECT Unit 57800; Ugo Basile, Comerio, Italy). A drop of 0.4% oxybuprocaine hydrochloride (Unicaine, Thea, France) is placed on the eyes before electrical stimulation. During the stimulation, mice are manually restrained and released into the observation cage (38×26×14 cm) immediately after the current application. The seizures are often preceded by a brief period (~2-3 s) of intense locomotor agitation (wild running and jumping). The animals then exhibit a "stunned" posture associated with rearing, forelimb automatic movements and clonus, twitching of the vibrissae, and Strub-tail. At the end of the seizure, animals resume their normal exploratory behavior. The experimental endpoint is protection against the seizure. The animal is considered to be protected if it resumes its normal exploratory behavior within 7 s from the stimulation.

In vivo activities determined for test compounds are typically comprised between 0.05 mg/kg and 10 mg/kg after single IP dosing.

6.2 Pentylenetetrazol (PTZ) Seizure Model

Pentylenetetrazol is used at the previously established $CD_{97}$ dose of 89 mg/kg; a convulsive dose inducing clonic convulsions of all four extremities in 97% of mice (Klitgaard et al., Eur. J. Pharmacol. (1998), 353, 191-206). Immediately following pentylenetetrazol injection the mice are placed individually in Perspex cages and observed for the presence of clonic convulsions in all four extremities and tonic hindlimb extension during 60 min period.

When tested, in vivo activities determined for the compounds of the accompanying Examples are typically comprised between 0.5 mg/kg and 30 mg/kg after single IP dosing.

3. Azamulin Assay

Cryopreserved human hepatocytes (pool of 20 donors, BSU batch from Celsis/IVT/Bioreclamation) were thawed accordingly the provider's information. Viability (trypan blue exclusion) was higher than 75%. Pre-incubations (250 µL of hepatocytes suspension at $2\times10^6$ hepatocytes/mL) were carried out with William's medium, containing 2 mM of glutamine and 15 mM of Hepes, in 48-well plates at +37° C., in an incubator (5% $CO_2$), under gentle agitation (vibrating agitator, Titramax 100, ca 300 rpm) during 30 min. After the pre-incubation, the incubation was initiated by adding to hepatocytes, 250 µL of culture medium (see composition above) containing UCB compound (1 µM) or midazolam (positive control) with or without azamulin (6 µM-specific CYP3A4/5 inhibitor). Final concentrations of UCB compound and azamulin in the incubates are 0.5 µM and 3 µM, respectively. The cell suspensions was rapidly re-homogenized by 2 in-out pipetting. After 0, 30, 60, 120, 180 and 240 minutes of incubation, reactions were stopped by transferring 50 µl of incubates into the appropriate well from 96-well plate containing 50 µL of ice cold acetonitrile with ketoconazole 1 µM as internal standard. Before each sampling, cell incubates are re-homogenized by 2 in out pipetting.

Once the incubation is finished, 96-well plates are centrifuged at ca 3700 rpm, +4° C., for 15 minutes. 50 µL of supernatants are transferred into the wells of other deep well plates to which 150 µL of $H_2O$ Millipore were added. These samples were are analyzed by micro UPLC/HR-MS for parent disappearance and monitoring of metabolite formation.

The CYP3A4/5 contribution known as fraction metabolized by CYP3A4/5 ($f_{m,CYP3A4/5}$) was calculated for each compound from the ratio between CLint (based on parent parent drug disappearance) in absence and in presence of azamulin, by using the following equation:

$$Fm_{CYP3A4/5} = 1 - CL_{int\ with\_1t}$$

When tested, the fraction metabolized by CYP3A4/5 ($f_{m,CYP3A4/5}$) of the compounds of the accompanying Examples is typically comprised between 0 and 45%.

Examples 5, 9, 13 and 16 exhibit a fraction metabolized by CYP3A4/5 ($f_{m,CYP3A4/5}$) comprised between 0 and 10%. Examples 1, 3, 6, 7, 8, 10, 15 and 20 exhibit a fraction metabolized by CYP3A4/5 ($f_{m,CYP3A4/5}$) greater than 10% and lower than or equal to 20%. Examples 2, 3, 11, 12, 14, 17-A and 17-B exhibit a fraction metabolized by CYP3A4/5 ($f_{m,CYP3A4/5}$) greater than 20% and lower than or equal to 45%.

The invention claimed is:

1. A compound according to formula (I), or a pharmaceutically acceptable salt thereof,

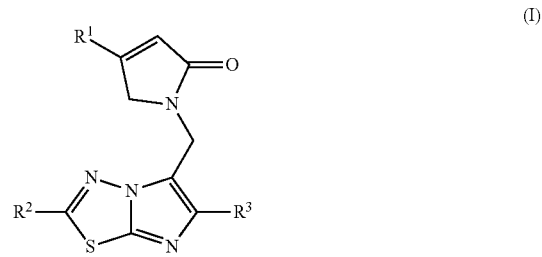

wherein

R$^1$ is a C$_{1-4}$ alkyl or a C$_{3-5}$ cycloalkyl, either of which groups are optionally substituted by one or more halogen substituents;

R$^2$ is a C$_{1-4}$ alkyl substituted by one hydroxy or alkoxy substituent;

R$^3$ is a halogen; or C$_{1-4}$ alkyl or C$_{3-4}$ cycloalkyl, either of which groups are optionally substituted by one or more halogen atoms.

2. A compound according to claim 1, or a pharmaceutically acceptable salt thereof, wherein R$^2$ is a C$_{1-4}$ alkyl substituted by a alkoxy substituent.

3. A compound according to claim 1, or a pharmaceutically acceptable salt thereof, wherein R$^3$ is a C$_{1-4}$ alkyl substituted by one or more halogen atoms.

4. A compound according to claim 1 or a pharmaceutically acceptable salt thereof, wherein R$^1$ is n-propyl, 2,2-difluoropropyl, 3,3,3-trifluoropropyl, 2-chloro-2,2-difluoroethyl, a 2,2,2-trifluoroethyl, or 2,2-difluorocyclopropyl.

5. A compound according to claim 1, or a pharmaceutically acceptable salt thereof, wherein R$^1$ is 3,3,3-trifluoropropyl, or 2,2-difluorocyclopropyl.

6. A compound according to claim 1, or a pharmaceutically acceptable salt thereof, wherein R$^2$ is a hydroxymethyl or a methoxymethyl.

7. A compound according to claim 1, or a pharmaceutically acceptable salt thereof wherein R$^2$ is a methoxymethyl.

8. A compound according to claim 1, or a pharmaceutically acceptable salt thereof, wherein R3 is a methyl, a difluoromethyl, a chlorine or a trifluoromethyl group.

9. A compound according to claim 1, or pharmaceutical acceptable salt thereof, wherein R3 is a methyl or difluoromethyl.

10. A compound according to claim 1 selected from the group consisting of:

1-[[2-(methoxymethyl)-6-(trifluoromethyl)imidazo[2,1-b][1,3,4]thiadiazol-5-yl]methyl]-3-propyl-2H-pyrrol-5-one;

1-[[2-(methoxymethyl)-6-(trifluoromethyl)imidazo[2,1-b][1,3,4]thiadiazol-5-yl]methyl]-3-(2,2,2-trifluoroethyl)-2H-pyrrol-5-one;

1-[[2-(methoxymethyl)-6-(trifluoromethyl)imidazo[2,1-b][1,3,4]thiadiazol-5-yl]methyl]-3-(3,3,3-trifluoropropyl)-2H-pyrrol-5-one;

1-[[2-(methoxymethyl)-6-methyl-imidazo[2,1-b][1,3,4]thiadiazol-5-yl]methyl]-3-propyl-2H-pyrrol-5-one;

1-[[6-chloro-2-(methoxymethyl)imidazo[2,1-b][1,3,4]thiadiazol-5-yl]methyl]-3-(2,2,2-trifluoroethyl)-2H-pyrrol-5-one;

1-[[6-chloro-2-(methoxymethyl)imidazo[2,1-b][1,3,4]thiadiazol-5-yl]methyl]-3-propyl-2H-pyrrol-5-one;

1-[[6-chloro-2-(methoxymethyl)imidazo[2,1-b][1,3,4]thiadiazol-5-yl]methyl]-3-(3,3,3-trifluoropropyl)-2H-pyrrol-5-one;

1-[[6-(difluoromethyl)-2-(methoxymethyl)imidazo[2,1-b][1,3,4]thiadiazol-5-yl]methyl]-3-propyl-2H-pyrrol-5-one;

1-[[6-(difluoromethyl)-2-(methoxymethyl)imidazo[2,1-b][1,3,4]thiadiazol-5-yl]methyl]-3-(2,2,2-trifluoroethyl)-2H-pyrrol-5-one;

1-[[6-(difluoromethyl)-2-(methoxymethyl)imidazo[2,1-b][1,3,4]thiadiazol-5-yl]methyl]-3-(2,2,2-trifluoroethyl)-2H-pyrrol-5-one;

1-[[2-(methoxymethyl)-6-methyl-imidazo[2,1-b][1,3,4]thiadiazol-5-yl]methyl]-3-(2,2,2-trifluoroethyl)-2H-pyrrol-5-one;

1-[[6-(difluoromethyl)-2-(methoxymethyl)imidazo[2,1-b][1,3,4]thiadiazol-5-yl]methyl]-3-(2,2,2-trifluoroethyl)-2H-pyrrol-5-one;

1-[[6-(1-fluorocyclopropyl)-2-(methoxymethyl)imidazo[2,1-b][1,3,4]thiadiazol-5-yl]methyl]-3-(2,2,2-trifluoroethyl)-2H-pyrrol-5-one;

3-(2-chloro-2,2-difluoro-ethyl)-1-[[2-(methoxymethyl)-6-(trifluoromethyl)imidazo[2,1-b][1,3,4]thiadiazol-5-yl]methyl]-2H-pyrrol-5-one;

1-[[2-(methoxymethyl)-6-methyl-imidazo[2,1-b][1,3,4]thiadiazol-5-yl]methyl]-3-(3,3,3-trifluoropropyl)-2H-pyrrol-5-one;

1-[[6-(difluoromethyl)-2-(methoxymethyl)imidazo[2,1-b][1,3,4]thiadiazol-5-yl]methyl]-3-(3,3,3-trifluoropropyl)-2H-pyrrol-5-one;

3-(2,2-difluoropropyl)-1-[[2-(methoxymethyl)-6-(trifluoromethyl)imidazo[2,1-b][1,3,4]thiadiazol-5-yl]methyl]-2H-pyrrol-5-one;

1-[[6-(difluoromethyl)-2-(methoxymethyl)imidazo[2,1-b][1,3,4]thiadiazol-5-yl]methyl]-3-(2,2-difluoropropyl)-2H-pyrrol-5-one;

3R-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one;

3S-(2,2-difluorocyclopropyl)-1-[[2-(methoxymethyl)-6-(trifluoromethyl)imidazo[2,1-b][1,3,4]thiadiazol-5-yl]methyl]-2H-pyrrol-5-one;

1-[[2-(methoxymethyl)-6-methyl-imidazo[2,1-b][1,3,4]thiadiazol-5-yl]methyl]-3R-[2,2-difluorocyclopropyl]-2H-pyrrol-5-one;

1-[[2-(methoxymethyl)-6-methyl-imidazo[2,1-b][1,3,4]thiadiazol-5-yl]methyl]-3S-[2,2-difluorocyclopropyl]-2H-pyrrol-5-one;

1-[[6-(difluoromethyl)-2-(methoxymethyl)imidazo[2,1-b][1,3,4]thiadiazol-5-yl]methyl]-3R-[2,2-difluorocyclopropyl]-2H-pyrrol-5-one;

1-[[6-(difluoromethyl)-2-(methoxymethyl)imidazo[2,1-b][1,3,4]thiadiazol-5-yl]methyl]-3S-[2,2-difluorocyclopropyl]-2H-pyrrol-5-one;

3-(2,2-difluoropropyl)-1-[[2-(methoxymethyl)-6-methyl-imidazo[2,1-b][1,3,4]thiadiazol-5-yl]methyl]-2H-pyrrol-5-one;

1-[[2-(hydroxymethyl)-6-methyl-imidazo[2,1-b][1,3,4]thiadiazol-5-yl]methyl]-3-(3,3,3-trifluoropropyl)-2H-pyrrol-5-one;

1-[[6-(difluoromethyl)-2-(hydroxymethyl)imidazo[2,1-b][1,3,4]thiadiazol-5-yl]methyl]-3-(3,3,3-trifluoropropyl)-2H-pyrrol-5-one; and 1-[[6-(difluoromethyl)-2-(hydroxymethyl)imidazo[2,1-b][1,3,4]thiadiazol-5-yl]methyl]-3-(2,2,2-trifluoroethyl)-2H-pyrrol-5-one.

11. A pharmaceutical composition comprising an effective amount of a compound according to claim 1 in combination with a pharmaceutically acceptable diluent or carrier.

12. A method for treatment of epilepsy, epileptogenesis, seizure disorders, convulsions comprising administering a compound according to claim 1 to a subject in need thereof.

13. A method for treatment of refractory seizures comprising administering a compound according to claim 1 to a subject in need thereof.

\* \* \* \* \*